(12) United States Patent
Faig et al.

(10) Patent No.: US 12,226,513 B2
(45) Date of Patent: *Feb. 18, 2025

(54) COSMETIC COMPOSITION CONTAINING A RHEOLOGICAL-MODIFYING AND STABILIZING POLYMER BLEND

(71) Applicant: L'OREAL, Paris (FR)

(72) Inventors: Jonathan Faig, Sayreville, NJ (US); Nicole Burkhard, Ledgewood, NJ (US); David Chan, Edison, NJ (US); Susan Halpern Chirch, Basking Ridge, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/852,525

(22) Filed: Jun. 29, 2022

(65) Prior Publication Data

US 2022/0409514 A1 Dec. 29, 2022

Related U.S. Application Data

(60) Provisional application No. 63/216,216, filed on Jun. 29, 2021.

(30) Foreign Application Priority Data

Aug. 26, 2021 (FR) ...................................... 2108952

(51) Int. Cl.
| | | |
|---|---|---|
| *A61K 8/44* | (2006.01) | |
| *A61K 8/04* | (2006.01) | |
| *A61K 8/34* | (2006.01) | |
| *A61K 8/368* | (2006.01) | |
| *A61K 8/49* | (2006.01) | |
| *A61K 8/73* | (2006.01) | |
| *A61K 8/81* | (2006.01) | |
| *A61Q 19/00* | (2006.01) | |

(52) U.S. Cl.
CPC ............ *A61K 8/8147* (2013.01); *A61K 8/042* (2013.01); *A61K 8/345* (2013.01); *A61K 8/368* (2013.01); *A61K 8/44* (2013.01); *A61K 8/4953* (2013.01); *A61K 8/735* (2013.01); *A61K 8/8152* (2013.01); *A61K 8/8188* (2013.01); *A61Q 19/00* (2013.01); *A61K 2800/48* (2013.01); *A61K 2800/524* (2013.01)

(58) Field of Classification Search
CPC .................................................. A61K 8/8147
See application file for complete search history.

(56) References Cited

U.S. PATENT DOCUMENTS

| | | | |
|---|---|---|---|
| 11,471,384 B2* | 10/2022 | Jouy | ....................... A61Q 19/00 |
| 2008/0025931 A1 | 1/2008 | Pelletier et al. | |
| 2008/0153839 A1 | 6/2008 | Cotton et al. | |
| 2012/0142788 A1 | 6/2012 | Koehler et al. | |
| 2013/0096208 A1 | 4/2013 | Koehler et al. | |
| 2015/0157539 A1 | 6/2015 | Shimizu et al. | |
| 2015/0174047 A1 | 6/2015 | Chiou et al. | |
| 2015/0174050 A1 | 6/2015 | Lu et al. | |
| 2016/0101139 A1 | 4/2016 | Paradise | |
| 2016/0101141 A1 | 4/2016 | Paradise | |
| 2016/0106797 A1 | 4/2016 | Paradise | |
| 2016/0106798 A1 | 4/2016 | Paradise | |
| 2016/0220308 A1 | 4/2016 | Khormaei et al. | |
| 2016/0220455 A1 | 4/2016 | Chiou et al. | |
| 2016/0220804 A1 | 4/2016 | Khormaei et al. | |
| 2016/0213599 A1 | 7/2016 | Devie | |
| 2016/0367470 A1 | 12/2016 | Chiou et al. | |
| 2017/0166673 A1 | 6/2017 | Huang et al. | |
| 2017/0326045 A1 | 11/2017 | Lorant et al. | |
| 2018/0028416 A1 | 2/2018 | Fu et al. | |
| 2018/0243182 A1 | 8/2018 | Ricard et al. | |
| 2018/0243189 A1 | 8/2018 | Pruns | |
| 2018/0344609 A1 | 12/2018 | Lu et al. | |
| 2018/0355112 A1 | 12/2018 | Zhang et al. | |
| 2018/0362697 A1 | 12/2018 | Huang et al. | |
| 2019/0110967 A1 | 4/2019 | Chiou | |
| 2019/0177460 A1 | 6/2019 | Huang et al. | |
| 2019/0240123 A1* | 8/2019 | Jouy | ....................... A61Q 19/00 |
| 2019/0336420 A1 | 11/2019 | Page et al. | |
| 2020/0253839 A1 | 8/2020 | Montoya | |

(Continued)

FOREIGN PATENT DOCUMENTS

| | | |
|---|---|---|
| CN | 110478264 A | 11/2019 |
| CN | 111388348 A | 7/2020 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

(Continued)

*Primary Examiner* — Nizal S Chandrakumar
(74) *Attorney, Agent, or Firm* — POLSINELLI PC

(57) ABSTRACT

The instant disclosure relates to a rheological-modifying and stabilizing polymer blend, cosmetic compositions comprising the polymer blend, and methods for stabilizing, for modifying viscosity, and for treating the skin using the polymer blend or using cosmetic compositions comprising the polymer blend. The rheological-modifying and stabilizing polymer blend comprises: (i) a carbomer; (ii) acrylates/C10-30 alkyl acrylate crosspolymer; and (iii) ammonium acryloyldimethyltaurate/steareth-25 methacrylate crosspolymer.

20 Claims, No Drawings

(56) References Cited

U.S. PATENT DOCUMENTS

| | | |
|---|---|---|
| 2021/0009743 A1 | 1/2021 | Huang et al. |
| 2021/0009762 A1 | 1/2021 | Zhang et al. |
| 2021/0015719 A1 | 1/2021 | Lu et al. |
| 2021/0093529 A1 | 4/2021 | LaRosa et al. |
| 2021/0093539 A1 | 4/2021 | LaRosa et al. |
| 2021/0186838 A1 | 6/2021 | Siefken et al. |
| 2021/0401715 A1 | 12/2021 | Faig et al. |

FOREIGN PATENT DOCUMENTS

| | | |
|---|---|---|
| CN | 112402310 A | 2/2021 |
| CN | 112773760 A | 5/2021 |
| CN | 114146034 A | 3/2022 |
| CN | 114177104 A | 3/2022 |
| FR | 3097433 A1 | 12/2020 |

OTHER PUBLICATIONS

"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Collier, Drug patents: the evergreening problem, CMAJ, Jun. 11, 2013, 185(9).*
Feldman, Understanding 'Evergreening': Making Minor Modifications Of Existing Medications To Extend Protections, Health Affairs Jun. 2022 41:6, 801-804.*
Odylique North America, 2024.*
Helenatur, p. 1-8, 2024.*
Preliminary Search Report and Written Opinion issued on May 5, 2022 for corresponding French Application No. FR 2108952.
Database GNPD; Mintel; Anonymous: "Ultimate Cellular Reviving Night Creme," 2009.
Anonymous: "Viscosity of Carbopol Polymers in Aqueous Sytems," Internet Citation; 2009 XP002713057.

* cited by examiner

COSMETIC COMPOSITION CONTAINING A RHEOLOGICAL-MODIFYING AND STABILIZING POLYMER BLEND

CROSS-REFERENCE TO RELATED APPLICATIONS

This application claims benefit of U.S. Ser. No. 63/216,216 filed Jun. 29, 2021, and benefit of French Application No. FR 2108952, filed on Aug. 26, 2021, which are incorporated herein by reference in their entirety.

FIELD OF THE DISCLOSURE

The instant disclosure relates to cosmetic compositions comprising a rheological-modifying and stabilizing polymer blend, and methods of treating the skin using the cosmetic compositions. In addition, the instant disclosure relates to methods for modifying a viscosity and/or for stabilizing a composition using the rheological-modifying and stabilizing polymer blend.

BACKGROUND OF THE DISCLOSURE

A common problem associated with formulating compositions, especially composition comprising active ingredients, is ensuring physical stability. Many active ingredients, including electrolytes, can cause stability problems, especially when used in high amounts. The consequence of stability problems is significant. For example, stability problems can cause partial, if not complete, loss of product integrity, color loss, malodor, viscosity changes, etc. With respect to active ingredients, stability problems reduce or eliminate activity, and prevent the active ingredients from reaching their intended target.

Many active ingredients, especially electrolytes, are unstable and sensitive to temperature, pH, light, and oxidation. Therefore, encapsulation processes have been employed to protect them from unwanted degradation and used for controlling release of the active ingredient. Antioxidants, for example, are substances that protect ingredients such as fragrances, natural fats, and oils from unstable molecules known as free radicals. Antioxidants interact with and stabilize free radicals and prevent damage caused by free radicals. Typically, antioxidants should be soluble in the ingredients that are protecting. Butylated hydroxytoluene (BHT), butylated hydroxyanisole (BHA), and tocopherols (Vitamin E) are common oil soluble antioxidants. Propyl gallate is an example of a water-soluble antioxidant.

Many ingredients in cosmetics, especially anti-aging and skin care products are unstable and break down quickly when exposed to atmospheric oxygen, light, or heat. To counter such break down, active ingredients have been incorporated into complexes for protection, e.g., complexed with cyclodextrin. For example, retinol is a useful anti-wrinkle ingredient that is sensitive to oxygen and light. Complexing retinol with cyclodextrin has been found to provide a stabilizing effect to the retinol.

High pressure homogenizers can be used in the processing of compositions, including cosmetic compositions, to form products such as emulsions, creams, sunscreens, makeups, and fragrances. Homogenization is widely used in the cosmetics industry to produce homogenous and stable emulsions. Through high pressure homogenization, particle sizes can be reduced to help avoid phrase separation, distribute various ingredients homogenously, and to modify viscosity.

Many cosmetic compositions for treating skin aim to provide active ingredients for absorption into the skin. Skin acts as a natural barrier between internal and external environments and therefore plays an important role in vital biological functions such as protection against mechanical and chemical injury, microorganisms, and ultraviolet damage. The health and appearance of skin, however, can deteriorate due to environmental factors, genetic makeup, nutrition, and sun exposure.

Environmental pollution conditions are fast worsening and becoming more apparent in the daily life of consumers worldwide. The damage of pollution against human skin is also becoming more and more evident. Human skin is also subjected to a variety of insults by extrinsic factors such as ultraviolet (UV) radiation, environmental pollution, wind, heat, infrared radiation, low humidity, harsh surfactants, abrasives, etc. Recent studies suggest that in addition to UV radiation, other environmental factors contribute to the development of solar lentigines, particularly air pollution. Ultimately, these factors result in visible signs of skin damage including small brown patches on the skin, especially in the elderly.

Typical skin damage includes fine lines, wrinkling, hyper-pigmentation, sallowness, sagging, dark under-eye circles, puffy eyes, enlarged pores, visible dead skin, i.e., flaking, scaling, dryness, and roughness. Consumers desire to slow the gaining of skin damage and reduce the effects of aging, especially in the face and around the eyes. Radiant and clear skin appears youthful and is a sign of good health and vitality. Accordingly, there is an ongoing need for new and improved formulations that improve the health and visual appearance of skin.

There is a need for compositions that are physically stable and effective. The inventors of the instant case found that a unique combination of certain polymers resulted in a rheological-modifying and stabilizing polymer blend. The rheological-modifying and stabilizing polymer blend is particularly well suited for use in cosmetic compositions, including cosmetic compositions for treating skin.

SUMMARY OF THE DISCLOSURE

The instant disclosure relates to cosmetic compositions comprising a rheological-modifying and stabilizing polymer blend (also referred to throughout the disclosure as simply "polymer blend"), and methods of treating the skin with the cosmetic compositions. The rheological-modifying and stabilizing polymer blend provides compositions with a desired viscosity and stabilizes the compositions, which allows the compositions to carry and deliver large loads of active ingredients. The instant disclosure also relates to the rheological-modifying and stabilizing polymer blends per se, and to methods for modifying viscosity and/or stabilizing compositions, such as cosmetic compositions, using the polymer blend.

The inventors discovered that a unique blend of three polymers interact with one another to dramatically improve stability and positively impact viscosity. The unique blend of polymers provides compositions containing high amounts of active ingredients with a surprising degree of stability without causing undue thickening. Often the amount of stabilizer(s) necessary to adequately stabilize a composition results in a product that is too viscous. If the amount of stabilizer(s) is reduced to generate a less viscous product, the stabilizing effects of the stabilizer(s) is not sufficient to maintain stability of the product. The polymer blends of the instant case successfully stabilize high amounts of active ingredients without unduly thickening the composition. The viscosity of the compositions can be easily modified to achieve a desired thickness without jeopardizing the integrity and stability of the final product.

The rheological-modifying and stabilizing polymer blend comprises:
(i) a carbomer;
(ii) acrylates/C10-30 alkyl acrylate crosspolymer; and
(iii) ammonium acryloyldimethyltaurate/steareth-25 methacrylate crosspolymer.

The amount of carbomer in the polymer blend is typically from about 25 to 75 wt. %, preferably from about 35 to about 65 wt. %, or more preferably, from about 40 to about 60 wt. %, based on the total weight of the rheological-modifying and stabilizing polymer blend.

The amount of acrylates/C10-30 alkyl acrylate crosspolymer in the polymer blend is typically from about 5 to about 50 wt. %, preferably from about 10 to about 40 wt. %, more preferably from about 15 to about 25 wt. %, based on the total weight of the rheological-modifying and stabilizing polymer blend.

The amount of ammonium acryloyldimethyltaurate/steareth-25 methacrylate crosspolymer in the polymer blend is typically from about 5 to about 50 wt. %, preferably from about 10 to about 40 wt. %, more preferably from about 15 to about 25 wt. %, based on the total weight of the rheological-modifying and stabilizing polymer blend.

In some instances, the total amount of (i) carbomer exceeds the individual amount of (ii) acrylates/C10-30 alkyl acrylate crosspolymer and/or exceeds the individual amount of (iii) ammonium acryloyldimethyltaurate/steareth-25 methacrylate crosspolymer in the polymer blend. Moreover, in some instances, the total amount of (i) carbomer exceeds the combined amount of (ii) acrylates/C10-30 alkyl acrylate crosspolymer and (iii) ammonium acryloyldimethyltaurate/steareth-25 methacrylate crosspolymer in the polymer blend. Further, in some instances, the weight ratio of (i) to ((ii)+(iii)) is from about 0.5:1 to about 2:1, preferably from about 0.7:1 to about 1.5:1, more preferably from about 0.8:1 to about 1.2:1, even more preferably about 1.1.

The rheological-modifying and stabilizing polymer blend may be incorporated into a composition comprising water (i.e., aqueous compositions), for instance, an aqueous cosmetic composition such as a cosmetic composition for application to the skin. Accordingly, the instant disclosure relates to a cosmetic composition comprising:
(a) a rheological-modifying and stabilizing polymer blend comprising:
    (i) a carbomer;
    (ii) acrylates/C10-30 alkyl acrylate crosspolymer; and
    (iii) ammonium acryloyldimethyltaurate/steareth-25 methacrylate crosspolymer; and
(b) water.

The amount of carbomer in the polymer blend included in the cosmetic composition is typically from about 25 to 75 wt. %, preferably from about 35 to about 65 wt. %, or more preferably, from about 40 to about 60 wt. %, based on the total weight of the rheological-modifying and stabilizing polymer blend.

The amount of acrylates/C10-30 alkyl acrylate crosspolymer in the polymer blend included in the cosmetic composition is typically from about 5 to about 50 wt. %, preferably from about 10 to about 40 wt. %, more preferably from about 15 to about 25 wt. %, based on the total weight of the rheological-modifying and stabilizing polymer blend.

The amount of ammonium acryloyldimethyltaurate/steareth-25 methacrylate crosspolymer in the polymer blend included in the cosmetic composition is typically from about 5 to about 50 wt. %, preferably from about 10 to about 40 wt. %, more preferably from about 15 to about 25 wt. %, based on the total weight of the rheological-modifying and stabilizing polymer blend.

In some instances, the total amount of (i) carbomer in the cosmetic composition exceeds the combined amount of (ii) acrylates/C10-30 alkyl acrylate crosspolymer and (iii) ammonium acryloyldimethyltaurate/steareth-25 methacrylate crosspolymer in the cosmetic composition. More typically, however, the weight ratio of (i) to ((ii)+(iii)) in the cosmetic composition may be from about 0.5:1 to about 2:1, preferably from about 0.7:1 to about 1.5:1, more preferably from about 0.8:1 to about 1.2:1, even more preferably about 1:1.

The cosmetic composition typically includes from about 0.1 to about 10 wt. %, preferably from about 0.5 to about 5 wt. %, more preferably from about 0.5 to about 2 wt. % of the polymer blend, based on the total weight of the cosmetic composition. The amounts of (i), (ii), and (iii) are set forth above with respect to the total weight of the total weight of the rheological-modifying and stabilizing polymer blend. However, the amounts of (i), (ii), and (iii) may also be defined relative to the total weight of the cosmetic composition, instead of the total weight of the rheological-modifying and stabilizing polymer blend, as illustrated below.

In some instances, the cosmetic composition comprises:
(a)(i) 0.1 to 8 wt. % of a carbomer;
(a)(ii) 0.05 to 5 wt. % of acrylates/C10-30 alkyl acrylate crosspolymer;
(a)(iii) 0.05 to 5 wt. % of ammonium acryloyldimethyltaurate/steareth-25 methacrylate crosspolymer; and
(b) 60 to 90 wt. % of water;
wherein all weight percentages are based on the total weight of the cosmetic composition.

The amount of carbomer in the cosmetic composition may be from about 0.1 to about 8 wt. %, preferably from about 0.1 to about 6 wt. %, more preferably from about 0.2 to about 5 wt. %, based on the total weight of the cosmetic composition.

The total amount of acrylates/C10-30 alkyl acrylate crosspolymer in the cosmetic composition may be from about 0.05 to about 5 wt. %, preferably from about 0.05 to about 4 wt. %, more preferably, from about 0.1 to about 2 wt. %, based on the total weight of the cosmetic composition.

The total amount of ammonium acryloyldimethyltaurate/steareth-25 methacrylate crosspolymer in the cosmetic composition may be from about 0.05 to about 5 wt. %, preferably from about 0.05 to about 4 wt. %, more preferably, from about 0.1 to about 2 wt. %, based on the total weight of the cosmetic composition.

In some instances, the total amount of (a)(i) carbomer in the cosmetic composition exceeds the combined amount of (a)(ii) acrylates/C10-30 alkyl acrylate crosspolymer and (a)(iii) ammonium acryloyldimethyltaurate/steareth-25 methacrylate crosspolymer in the cosmetic composition. More typically, however, the weight ratio of (a)(i) to (a)((ii)+(a)(iii)) in the cosmetic composition may be from about 0.5:1 to about 2:1, preferably from about 0.7:1 to about 1.5:1, more preferably from about 0.8:1 to about 1.2:1, even more preferably about 1:1.

The pH of the cosmetic composition may vary. In some instances, the pH of the cosmetic composition may be from about 5 to about 9, preferably from about 5.5 to about 8, more preferably from about 5.5 to about 7 or from 5.5 to less than 7. In some instances, the pH of the cosmetic composition is less than 7, for example, 6.8 or less, 6.5 or less, 6.2 or less, or 6 or less.

The cosmetic composition may be in a variety of different forms, for example, a gel, an emulsion, a lotion, a cream, etc. Preferably, the cosmetic composition is in the form of a gel or in the form of an emulsion, particularly an oil-in-water emulsion. When the cosmetic composition is in the form of a gel, emulsifiers and/or surfactants may not be required, i.e., the cosmetic composition may be free of emulsifiers and/or surfactants. Nonetheless, in some instances the gel may include emulsifiers and/or surfactants.

When the cosmetic composition is in the form of an emulsion, the cosmetic composition will typically include one or more fatty compounds (to form a fatty phase) and one or more emulsifiers and/or surfactants. The fatty compounds may include silicones, but in some instances the fatty compounds are not, and do not include silicones such as crosslinked siloxane elastomers. Moreover, the cosmetic compositions may be free or essentially free from silicones including crosslinked siloxane elastomers. The emulsifiers and/or surfactants are useful for emulsifying the cosmetic compositions.

In some instances, the cosmetic composition includes from about 1 to about 40 wt. %, preferably from about 1 to about 30 wt. %, more preferably from about 1 to about 25 wt. %, even more preferably from about 2 to about 15 wt. % of one or more fatty compounds.

The cosmetic compositions may include from about 0.1 to about 10 wt. %, preferably from about 0.1 to about 8 wt. %, more preferably from about 0.1 to about 6 wt. %, even more preferably from about 0.2 to about 4 wt. % of one or more emulsifiers and/or surfactants. Non-limiting examples of emulsifiers include glyceryl esters and derivatives, alkoxylated carboxylic acids (e.g., PEG-30 dipolyhydroxystearate), oxyalkylenated fatty acid esters of glycerol, oxyalkylenated fatty acid esters of sorbitan, oxyalkylenated fatty acid esters, oxyalkylenated fatty alkyl ethers, sugar esters (e.g., arachidyl glucoside), and mixtures thereof.

The cosmetic compositions may further include one or more water-soluble solvents. Non-limiting examples include glycols, glycerin, $C_1$-$C_4$ alcohols, polyhydric alcohols, and a mixture thereof. For instance, the total amount of water-soluble solvents in the cosmetic composition may be from about 1 to about 40 wt. %, preferably from about 1 to about 30 wt. %, more preferably from about 5 to about 25 wt. %, even more preferably from about 10 to about 25 wt. %, based on the total weight of the cosmetic composition.

The viscosity of the cosmetic compositions may vary and may be adjusted depending on the desired form and properties of composition. Nonetheless, in some instances, the viscosity of the cosmetic compositions may be from about 5,000 cP to about 100,000 cP at 25° C. The viscosity can be measured using a Brooksfield DV-1 Viscometer with a T-bar spindle, reading at 30 seconds and 10 rpm. In some instances, the viscosity of the cosmetic compositions may be from about 5,000 cP to about 80,000 cP, about 5,000 cP to about 50,000 cP, about 5,000 cP to about 25,000 cP, about 5,000 cP to about 10,000 cP, 10,000 cP to about 100,000 cP, about 25,000 cP to about 100,000 cP, about 50,000 to about 100,000 cP, about 75,000 cP to about 100,000 cP, about 10,000 cP to about 90,000 cP, about 25,000 cP to about 75,000 cP, or about 30,000 cP to about 60,000 cP at 25° C.

As already noted, the polymer blends of the instant case are particularly well suited for use in cosmetic compositions, in particular, cosmetic composition comprising one or more active ingredients, preferably, one or more active ingredients for treating skin (skin active ingredients). Non-limiting examples of skin active ingredients include anti-aging agents, depigmenting agents, anti-wrinkle agents, agent that treat oily skin, mattifying agents, antioxidants, vitamins, anti-acne agents, anti-inflammatory agents, and electrolytes. In some instances, it is preferable that the one or more skin active ingredients are chosen from C-glycoside derivatives (e.g., hydroxypropyl tetrahydropyrantriol), a hyaluronic acid or derivative thereof (e.g., sodium hyaluronate), salicylic acid or derivative thereof (e.g., capryloyl salicylic acid), an ester thereof, or a salt thereof.

The total amount of skin active ingredients in the cosmetic compositions can vary. Nonetheless, in some instances, the total amount of skin active ingredients is from about 0.1 to about 20 wt. %, preferably from about 0.5 to about 15 wt. %, more preferably from about 1 to about 15 wt. %, even more preferably from about 1 to about 10 wt. %, based on the total weight of the cosmetic composition.

The instant disclosure relates to methods of stabilizing and/or modifying the viscosity of a composition, for example, a cosmetic composition such as a cosmetic composition for treating the skin. The method of stabilizing and/or modifying the viscosity of a composition, including cosmetic compositions, include incorporating the rheological-modifying and stabilizing polymer blend as described herein into the composition. The rheological-modifying and stabilizing polymer blend is used in amounts sufficient to stabilize and/or modify the viscosity of the composition. For example, the rheological-modifying and stabilizing polymer blend may be added in amounts from about 0.1 to about 10 wt. %, preferably from about 0.5 to about 5 wt. %, more preferably from about 0.5 to about 2 wt. % of the polymer blend, based on the total weight of the composition. The methods relate to stabilizing one or more active ingredients in the composition. The one or more active ingredients may be included in various amounts depending on the active ingredient to be stabilized and the desired amount of active ingredient to be included in the composition. Nonetheless, the total amount of active ingredients in the cosmetic compositions can vary. Nonetheless, in some instances, the total amount of active ingredients, such as skin active ingredients, may be from about 0.1 to about 20 wt. %, preferably from about 0.5 to about 15 wt. %, more preferably from about 1 to about 15 wt. %, even more preferably from about 1 to about 10 wt. %, based on the total weight of the cosmetic composition.

Finally, the instant disclosure relates to treating skin using the cosmetic compositions described herein. The methods involve applying the cosmetic composition to the skin, for example, the skin of the face. In some instances, the cosmetic composition may remain on the face (a leave-on product). In other cases, however, the cosmetic composition may be rinsed from the face after application to the skin for a period of time (a rinse-off product).

DETAILED DESCRIPTION OF THE DISCLOSURE

The rheological-modifying and stabilizing polymer blends according to the instant disclosure include:
(i) a carbomer;
(ii) acrylates/C10-30 alkyl acrylate crosspolymer; and
(iii) ammonium acryloyldimethyltaurate/steareth-25 methacrylate crosspolymer.

Carbomer is a term used for a series of polymers made from acrylic acid. Therefore, the term carbomer is equivalent to the term poly(acrylic acid) (PAA), a high-molecular weight polymer of acrylic acid. The IUPAC name is poly (1-carboxyethylene). They may be homopolymers of acrylic acid, or crosslinked with an allyl ether of pentaerythritol, allyl ether of sucrose, or allyl ether of propylene. In a water solution at neutral pH, PAA is an anionic polymer, i.e. many of the side chains of PAA will lose their protons and acquire a negative charge. A particularly preferred carbomer for use in the polymer blends and compositions of the instant case is SYNTHALEN K produced by 3V, having the INCI name "carbomer."

The amount of carbomer in the rheological-modifying and stabilizing polymer blend may vary. In some instances, the total amount of carbomer in the polymer blend is from about 25 to 75 wt. %, based on the total weight of the rheological-modifying and stabilizing polymer blend. In some cases, the total amount of carbomer in the rheological-modifying and stabilizing polymer blend is from about 20 to 70 wt. %, about 30 to about 70 wt. %, about 35 to about 65 wt. %, about 40 to about 60 wt. %, based on the total weight of the rheological-modifying and stabilizing polymer blend.

Acrylates/C10-30 alkyl acrylate crosspolymer is a co-polymer. The formation of acrylates/C10-30 alkyl acrylate crosspolymer occurs when 010-30 acrylate is combined with monomers of acrylic acid and methacrylic acid. While carbomers are polymers of acrylic acid monomers, acrylates/C10-30 alkyl acrylate crosspolymer is comprised of a mixture of acrylic acid and methacrylic acid. A particularly preferred acrylates/C10-30 alkyl acrylate crosspolymer for use in the polymer blends and compositions of the instant case is CARBOPOL ULTREZ-21 available from Lubrizol, having the INCI name: "acrylates/C10-30 alkyl acrylate crosspolymer."

The amount of acrylates/C10-30 alkyl acrylate crosspolymer in the rheological-modifying and stabilizing polymer blend may vary. In some instances, the total amount of the acrylates/C10-30 alkyl acrylate crosspolymer in the rheological-modifying and stabilizing polymer blend is from about 5 to about 50 wt. %, based on the total weight of the rheological-modifying and stabilizing polymer blend. In some instances, the total amount of the acrylates/C10-30 alkyl acrylate crosspolymer in the rheological-modifying and stabilizing polymer blend is from about 10 to about 40 wt. %, about 10 to about 30 wt. %, about 20 to about 40 wt. %, about 15 to about 35 wt. %, about 20 to about 30 wt. %, or about 22 to about 28 wt. %, based on the total weight of the rheological-modifying and stabilizing polymer blend.

Ammonium acryloyldimethyltaurate/steareth-25 methacrylate crosspolymer is also referred to as 1-propapnesulfonic acid, 2-methyl-2-[(1-oxo-2-propenyl)amino]-, monoammonium salt, polymers with docosylpoly(oxyethylene) 2-methyl-2-propenoate (25 mol EO average). It is a copolymer of ammonium acryloyldimethyltaurate and steareth-25 methacrylate monomers. Ammonium acryloyldimethyltaurate/steareth-25 methacrylate crosspolymer for use in the polymer blends and compositions of the instant case can be obtained from Clairant with the tradename ARISTOFLEX HMS, having the INCI name: "ammonium acryloyldimethyltaurate/steareth-25 methacrylate crosspolymer."

The amount of ammonium acryloyldimethyltaurate/steareth-25 methacrylate crosspolymer in the rheological-modifying and stabilizing polymer blend may vary. In some instances, the total amount of the acryloyldimethyltaurate/steareth-25 methacrylate crosspolymer in the rheological-modifying and stabilizing polymer blend is from about 5 to about 50 wt. %, based on the total weight of the rheological-modifying and stabilizing polymer blend. In some instances, the total amount of the ammonium acryloyldimethyltaurate/ steareth-25 methacrylate crosspolymer in the rheological-modifying and stabilizing polymer blend is from about 10 to about 40 wt. %, about 10 to about 30 wt. %, about 20 to about 40 wt. %, about 15 to about 35 wt. %, about 20 to about 30 wt. %, or about 22 to about 28 wt. %, based on the total weight of the rheological-modifying and stabilizing polymer blend.

The amounts of (i) carbomer, (ii) acrylates/C10-30 alkyl acrylate crosspolymer, and (iii) ammonium acryloyldimethyltaurate/steareth-25 methacrylate crosspolymer in the rheological-modifying and stabilizing polymer blend can vary with respect to one another. For example, in some instances, the total amount of (i) carbomer is greater than the individual amount of (ii) acrylates/C10-30 alkyl acrylate crosspolymer and/or greater than the individual amount of (iii) ammonium acryloyldimethyltaurate/steareth-25 methacrylate crosspolymer. However, the total amount of (i) carbomer can be greater than the combined amounts of (ii) acrylates/C10-30 alkyl acrylate crosspolymer and (iii) ammonium acryloyldimethyl-taurate/steareth-25 methacrylate crosspolymer. In some instances, the weight ratio of (i) to ((ii)+(iii)) is from about 0.5:1 to about 2:1. Nonetheless, in some instances, the weight ratio of (i) to ((ii)+(iii)) is from about 0.5:1 to about 1.9:1, about 0.5:1 to about 1.8:1, about 0.5:1 to about 1.6:1, about 0.6:1 to about 1.5:1, about 0.7:1 to about 1.4:1, about 0.8:1 to about 1.3:1, about 0.9:1 to about 1.2:1, about 0.9:1 to about 1.1:1, or about 1:1.

The rheological-modifying and stabilizing polymer blend may be incorporated into a composition comprising water (an aqueous composition), for instance, a cosmetic composition including a cosmetic composition for application to the skin. Thus, compositions according to the instant disclosure include:

(a) a rheological-modifying and stabilizing polymer blend comprising:
  (i) a carbomer;
  (ii) acrylates/C10-30 alkyl acrylate crosspolymer; and
  (iii) ammonium acryloyldimethyltaurate/steareth-25 methacrylate crosspolymer; and
(b) water.

The amounts the polymers ((i), (ii), and (iii)) in the composition comprising water may be in accordance with the amounts set forth above, relative to the total weight of the rheological-modifying and stabilizing polymer blend. The ratio of the polymers ((i), (ii), and (iii)) in the composition comprising water may also be in accordance with the ratios set forth above.

The amount of carbomer in the cosmetic composition may vary. In some instances, the amount of carbomer in the cosmetic composition may be from about 0.1 to about 10 wt. %, based on the total weight of the cosmetic composition. In addition, in some instances, the amount of carbomer may be from about 0.1 to about 8 wt. %, about 0.1 to about 6 wt. %, about 0.1 to about 5 wt. %, about 0.1 to about 4 wt. %, about 0.1 to about 2 wt. %, about 0.2 to about 10 wt. %, about 0.2 to about 8 wt. %, about 0.2 to about 6 wt. %, about 0.2 to about 5 wt. %, about 0.2 to about 4 wt. %, about 0.2 to about 2 wt. %, about 0.5 to about 10 wt. %, about 0.5 to about 8 wt. %, about 0.5 to about 5 wt. %, about 0.5 to about 4 wt. %, or about 0.5 to about 2 wt. %, based on the total weight of the cosmetic composition.

The total amount of acrylates/C10-30 alkyl acrylate crosspolymer in the cosmetic composition may vary. In some instances, the total amount of acrylates/C10-30 alkyl acrylate crosspolymer in the cosmetic composition is about 0.05 to about 5 wt. %. In addition, in some instances, the total amount of acrylates/C10-30 alkyl acrylate crosspolymer is about 0.05 to about 4 wt. %, about 0.05 to about 3 wt. %, about 0.05 to about 2 wt. %, 0.05 to about 1 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.2 to about 5 wt. %, about 0.2 to about 4 wt. %, about 0.2 to about 3 wt. %, about 0.2 to about 2 wt. %, or about 0.2 to about 1 wt. %, based on the total weight of the cosmetic composition.

The total amount of ammonium acryloyldimethyltaurate/steareth-25 methacrylate crosspolymer in the cosmetic composition may vary. In some instances, the total amount of ammonium acryloyldimethyltaurate/steareth-25 methacrylate crosspolymer in the cosmetic composition is about 0.05 to about 5 wt. %. In addition, in some instances, the total amount of ammonium acryloyldimethyltaurate/steareth-25 methacrylate crosspolymer is about 0.05 to about 4 wt. %, about 0.05 to about 3 wt. %, about 0.05 to about 2 wt. %, 0.05 to about 1 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.2 to about 5 wt. %, about 0.2 to about 4 wt. %, about 0.2 to about 3 wt. %, about 0.2 to about 2 wt. %, or about 0.2 to about 1 wt. %, based on the total weight of the cosmetic composition.

The amount of water in the cosmetic composition may vary. In some instances, the total amount of water in the cosmetic composition is from about 50 to about 95 wt. % water. In addition, in some instances, the total amount of water in the cosmetic composition is from about 50 to about 90 wt. %, from about 50 to about 85 wt. %, about 50 to about 80 wt. %, about 60 to about 95 wt. %, about 60 to about 90 wt. %, about 60 to about 85 wt. %, about 60 to about 80 wt. %, about 65 to about 95 wt. %, about 65 to about 90 wt. %, or about 65 to about 85 wt. %, based on the total weight of the cosmetic composition.

In some instances, the total amount of (a)(i) carbomer in the cosmetic composition exceeds the individual amount of (a)(ii) acrylates/C10-30 alkyl acrylate crosspolymer and/or the individual amount of (a)(iii) ammonium acryloyldimethyltaurate/steareth-25 methacrylate crosspolymer in the cosmetic composition. Furthermore, the total amount of (a)(i) carbomer in the cosmetic composition may exceed the combined amount of (a)(ii) acrylates/C10-30 alkyl acrylate crosspolymer and (a)(iii) ammonium acryloyldimethyltaurate/steareth-25 methacrylate crosspolymer in the cosmetic composition. In some instances, the weight ratio of ((a)i) to ((a)(ii)+(a)(iii)) is from about 0.5:1 to about 2:1. Nonetheless, in some instances, the weight ratio of ((a)(i) to ((a)(ii)+(a)(iii)) is from about 0.5:1 to about 1.9:1, about 0.5:1 to about 1.8:1, about 0.5:1 to about 1.6:1, about 0.6:1 to about 1.5:1, about 0.7:1 to about 1.4:1, about 0.8:1 to about 1.3:1, about 0.9:1 to about 1.2:1, about 0.9:1 to about 1.1:1, or about 1:1.

The pH of the cosmetic composition may vary. In some instances, the pH of the cosmetic composition is from about 5 to about 9. Moreover, in some cases, the pH of the cosmetic composition is from 5 to 8, 5 to 7, about 5.5 to about 9, about 5.5 to about 8, about 5.5 to about 7, about 6 to about 9, about 6 to about 8, or about 6 to about 7. Furthermore, in some instances, the pH of the cosmetic composition is below 7, for example, 6.8 or less, 6.5 or less, 6.2 or less, or 6 or less.

The cosmetic composition may be in a variety of different forms, for example, a gel, an emulsion, a lotion, a cream, etc. Preferably, the cosmetic composition is in the form of a gel or in the form of an emulsion, particularly an oil-in-water emulsion. When the cosmetic composition is in the form of a gel, emulsifiers and/or surfactants may not be required, i.e., the cosmetic composition may be free of emulsifiers and/or surfactants. Nonetheless, in some instances the gel may include emulsifiers and/or surfactants.

When the cosmetic composition is in the form of an emulsion, the cosmetic composition will typically include one or more fatty compounds (to form a fatty phase) and one or more emulsifiers and/or surfactants (to incorporate the fatty phase and an aqueous phase). The fatty compounds may include silicones, but in some instances the fatty compounds are free from silicones. Moreover, the cosmetic composition may be free or essentially free from silicones. The emulsifiers and/or surfactants are useful for emulsifying the cosmetic composition.

Non-limiting examples of fatty compounds include fatty alcohols, fatty acids, fatty esters, oils, waxes, triglycerides, derivatives thereof, and mixtures thereof. In certain instances, the fatty ester may be chosen from ethoxylated fatty esters, sorbitan fatty esters, esters of stearates, esters of behenates, esters of arachidates, esters of palmitates, fatty acid esters of a sugar, and mixtures thereof. In further instances, the fatty ester chosen from purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, and pentaerythritol esters, and mixtures thereof. The fatty compounds may comprise one or more fatty alcohols (e.g., arachidyl alcohol, behenyl alcohol, cetearyl alcohol, etc.), one or more triglycerides (e.g., caprylic/capric triglyceride), isononyl isononanoate, cetyl ethylhexanoate, and mixtures thereof. A more exhaustive list of useful fatty compounds is set forth below under the heading "Fatty Compounds."

The total amount of fatty compounds in the cosmetic composition may vary. In some instances, the cosmetic composition includes from about 1 to about 40 wt. % of the one or more fatty compounds. Moreover, in some cases the cosmetic composition comprises from about 1 to about 30 wt. %, about 1 to about 25 wt. %, about 1 to about 20 wt. %, about 1 to about 15 wt. %, about 1 to about 10 wt. %, about 2 to about 40 wt. %, about 2 to about 30 wt. %, about 2 to about 25 wt. %, about 2 to about 20 wt. %, about 2 to about 15 wt. %, about 2 to about 10 wt. %, about 5 to about 40 wt. %, about 5 to about 30 wt. %, about 5 to about 25 wt. %, about 5 to about 20 wt. %, or about 5 to about 15 wt. %, based on the total weight of the cosmetic composition.

Emulsifiers are, typically, used to incorporate the oil and/or fatty compounds into a hydrophilic medium, such as an aqueous medium, to form oil-in-water emulsions. In some instances, however, the emulsifiers may be used to incorporate a hydrophilic phase (e.g., aqueous medium) into an oil or fatty phase to form a water-in-oil emulsion. The constituents categorized as emulsifiers overlaps with the constituents categorized as surfactants, especially nonionic surfactants. In other words, many compounds that function as emulsifiers also function as surfactants and vice versa.

The cosmetic compositions typically include one or more emulsifiers and/or surfactants, for example, one or more nonionic emulsifiers (and/or nonionic surfactants). Additional useful emulsifiers or surfactants include amphoteric, anionic, and/or cationic emulsifiers and surfactants.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof. A more exhaustive but non-limiting list of useful nonionic emulsifiers is provided later, under the heading "Nonionic Emulsifiers."

In some cases, it is preferable that cosmetic compositions containing natural oils include two or more nonionic emulsifiers. In particular, one or more nonionic emulsifier having an HLB of 10 or higher and one or more nonionic emulsifiers having an HLB of 5 or less. The total amount of these emulsifiers can be such that the final HLB of the hair-treatment composition is within +/−0.5 of the HLB of the natural oil in the cosmetic composition. This typically results in the final HLB of the emulsified natural oil in the hair-treatment composition ranging from about 6 to about 8.

Non-limiting examples of emulsifiers include glyceryl esters and derivatives, alkoxylated carboxylic acids (PEG-30 dipolyhydroxystearate), oxyalkylenated fatty acid esters of glycerol, oxyalkylenated fatty acid esters of sorbitan, oxyalkylenated fatty acid esters, oxyalkylenated fatty alkyl ethers, sugar esters (arachidyl glucoside), and mixtures thereof.

Additional non-limiting examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

Preferably, the cosmetic composition includes a nonionic emulsifier chosen from polyglyeryl-based emulsifiers, polyol esters, glycerol ethers, oxyethylenated ethers, oxypropylenated ethers, ethylene glycol polymers, sorbitan esters, polysorbate, and mixtures thereof. In some instances, the one or more nonionic emulsifier selected from polyglyceryl 10-stearate, polyglyceryl-3-caprate, polyglyceryl-3-diisostearate, polyglyceryl-3 methylglucose distearate, and mixtures thereof. In some instances, the cosmetic composition includes cetearyl glucoside, trideceth-6, PEG-30 dipolyhydroxystearate, and arachidyl glucoside.

A more exhaustive but non-limiting list of nonionic surfactants that may be included in the cosmetic compositions is set forth later, under the heading "Nonionic Surfactants."

The amounts of emulsifiers and/or surfactants that may be included in the cosmetic compositions can vary. Nonetheless, in some instances, the total amount of emulsifiers and/or surfactants is from about 0.05 to about 10 wt. %, based on the total weight of the cosmetic composition. Moreover, in some instances, the total amount of emulsifiers and/or surfactants in the cosmetic compositions may be from about 0.05 to about 8 wt. %, about 0.05 to about 6 wt. %, about 0.05 to about 5 wt. %, about 0.1 to about 10 wt. %, about 0.1 to about 8 wt. %, about 0.1 to about 6 wt. %, about 0.1 to about 5 wt. %, about 0.1 to about 3 wt. %, or about 0.1 to about 2 wt. %, based on the total weight of the cosmetic composition.

The cosmetic compositions typically include one or more water-soluble solvents. Non-limiting examples include glycols, glycerin, $C_1$-$C_4$ alcohols, polyhydric alcohols, and a mixture thereof. A more exhaustive but non-limiting list of useful water-soluble solvents is provided later, under the heading "Water-Soluble Solvents."

The total amount of water-soluble solvents can vary. Nonetheless, the amount of water-soluble solvent is typically from about 1 to about 40 wt. %, based on the total weight of the cosmetic composition. Moreover, in some instances, the total amount of water-soluble solvent may be from about 1 to about 35 wt. %, about 1 to about 30 wt. %, about 1 to about 25 wt. %, about 1 to about 20 wt. %, about 5 to about 40 wt. %, about 5 to about 35 wt. %, about 5 to about 30 wt. %, about 5 to about 25 wt. %, about 5 to about 20 wt. %, or about 10 to about 20 wt. %, based on the total weight of the cosmetic composition.

The viscosity of the cosmetic compositions may vary, and may be adjusted depending on the desired form and properties of composition. Nonetheless, in some instances, the viscosity of the cosmetic composition may be from about 5,000 cP to about 100,000 cP at 25° C. The viscosity can be measured using a Brooksfield DV-1 Viscometer with a T-bar spindle, reading at 30 seconds and 10 rpm. In some instances, the viscosity of the cosmetic compositions may be from about 5,000 cP to about 80,000 cP, about 5,000 cP to about 50,000 cP, about 5,000 cP to about 25,000 cP, about 5,000 cP to about 10,000 cP, 10,000 cP to about 100,000 cP, about 25,000 cP to about 100,000 cP, about 50,000 to about 100,000 cP, about 75,000 cP to about 100,000 cP, about 10,000 cP to about 90,000 cP, about 25,000 cP to about 75,000 cP, or about 30,000 cP to about 60,000 cP at 25° C.

As already noted, the polymer blends of the instant case is particularly well suited for use in cosmetic compositions, in particular, cosmetic composition comprising one or more active ingredients, preferably, one or more skin active ingredients. Accordingly, the cosmetic compositions of the instant case typically include one or more active ingredients, in particular, one or more skin active ingredients. Non-limiting examples of skin active ingredients include anti-aging agents, depigmenting agents, anti-wrinkle agents, agent that treat oily skin, mattifying agents, antioxidants, vitamins, anti-acne agents, anti-inflammatory agents, and electrolytes. In some instances, it is preferable that the one or more skin active ingredients are chosen from a C-glycoside derivative (e.g., hydroxypropyl tetrahydropyrantriol), a hyaluronic acid or derivative thereof (e.g., sodium hyaluronate), salicylic acid or a derivative thereof (e.g., capryloyl salicylic acid), an ester thereof, or a salt thereof.

The total amount of skin active ingredients in the cosmetic compositions can vary. Nonetheless, in some instances, the total amount of skin active ingredients is from about 0.1 to about 20 wt. %, based on the total weight of the cosmetic composition. Moreover, in some cases, the total amount of skin active ingredients in the cosmetic composition may be from about 0.1 to about 15 wt. %, about 0.1 to about 10 wt. %, about 0.1 to about 5 wt. %, about 0.2 to about 20 wt. %, about 0.2 to about 15 wt. %, about 0.2 to about 10 wt. %, about 0.2 to about 5 wt. %, about 0.5 to about 20 wt. %, about 0.5 to about 15 wt. %, about 0.5 to about 10 wt. %, about 0.5 to about 5 wt. %, about 1 to about 20 wt. %, about 1 to about 15 wt. %, about 1 to about 10 wt. %, about 1 to about 5 wt. %, about 2 to about 10 wt. %, about 2 to about 8 wt. %, or about 2 to about 6 wt. %, based on the total weight of the cosmetic composition.

The instant disclosure relates to methods of stabilizing and/or modifying the viscosity of a composition, for example, a cosmetic composition such as a cosmetic composition for treating the skin. The method of stabilizing and/or modifying the viscosity of a composition, including a cosmetic composition such as a cosmetic composition for treating the skin, include incorporating the rheological-modifying and stabilizing polymer blend as described herein into a composition, for example, a cosmetic composition such as a cosmetic composition for treating the skin. The rheological-modifying and stabilizing polymer blend is used in amount sufficient to stabilize and/or modify the viscosity of the composition. For example, the rheological-modifying and stabilizing polymer blend may be added in amounts from about 0.1 to about 10 wt. %, preferably from about 0.5 to about 5 wt. %, more preferably from about 0.5 to about 2 wt. % of the polymer blend, based on the total weight of the composition. The methods relate to stabilizing one or more active ingredients in the composition. The one or more active ingredients may be included in various amounts depending on the active ingredient to be stabilized and the desired amount of active ingredient to be included in the composition. Nonetheless, the total amount of active ingredients in the cosmetic compositions can vary. Nonetheless, in some instances, the total amount of active ingredients, such as skin active ingredients, may be from about 0.1 to about 20 wt. %, preferably from about 0.5 to about 15 wt. %, more preferably from about 1 to about 15 wt. %, even more preferably from about 1 to about 10 wt. %, based on the total weight of the cosmetic composition.

Finally, the instant disclosure relates to treating skin using the cosmetic compositions described herein. The methods involve applying the cosmetic composition to the skin, for example, the skin of the face. In some instances, the cosmetic composition may remain on the face (a leave-on product). In other cases, however, the cosmetic composition may be rinsed from the face after application to the skin for a period of time (a rinse-off product).

Fatty Compounds

Fatty compounds include, for example, oils. Non-limiting examples of oils include silicone oils, fluoro oils, hydrocarbon-based oils, etc. In some instances, the cosmetic composition includes oils that are plant based or vegetable-based oils. The amount of oil and/or plant based or vegetable based oil present in the cosmetic composition may be from about 0.1 to about 10 wt. %, about 0.1 to about 8 wt. %, about 0.1 to about 7 wt. %, about 0.1 to about 6 wt. %, about 0.1 to about 5 wt. %; about 0.5 to about 10 wt. %, about 0.5 to about 8 wt. %, about 0.5 to about 7 wt. %, about 0.5 to about 6 wt. %, about 0.5 to about 5 wt. %; about 1 to about 10 wt. %, about 1 to about 8 wt. %, about 1 to about 7 wt. %, about 1 to about 6 wt. %, about 1 to about 5 wt. %; about 2 to about 10 wt. %, about 2 to about 8 wt. %, about 2 to about 7 wt. %, about 2 to about 6 wt. %, about 2 to about 5 wt. %; about 3 to about 10 wt. %, about 3 to about 8 wt. %, about 3 to about 7 wt. %, about 3 to about 6 wt. %, about 3 to about 5 wt. %; about 4 to about 10 wt. %, about 4 to about 8 wt. %, or about 4 to about 7 wt. %, including all ranges and sub-ranges there between, based on the total weight of the cosmetic composition.

Additionally, and/or alternatively, the cosmetic composition may exclude synthetic oils. In some case, the cosmetic composition may exclude oils other than plant based and vegetable-based oils. For example, the amount of synthetic oils and/or oils other than plant based and vegetable based oil may be about 5 wt. % or less, about 4 wt. % or less, about 3 wt. % or less, about 2 wt. % or less, about 1 wt. % or less, about 0.5 wt. % or less, about 0.1 or less, or about 0.05 or less based on the total weight of the cosmetic composition. In at least one embodiment, the cosmetic composition is free of or essentially free of synthetic oils and/or oils other than plant based and vegetable based oil. In at least one embodiment, the cosmetic composition is free of or essentially free of silicone oils. In some instances, the amount of silicone oils may be about 5 wt. % or less, about 4 wt. % or less, about 3 wt. % or less, about 2 wt. % or less, about 1 wt. % or less, about 0.5 wt. % or less, about 0.1 or less, or about 0.05 or less based on the total weight of the cosmetic composition.

The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. Oil that is suitable for use herein may be volatile or non-volatile. The term "volatile oil" relates to an oil that is capable of evaporating on contact with the skin or a keratin fiber in less than one hour, at room temperature and atmospheric pressure. Volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to an oil that remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes ($8\times10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

Fluoro Oils

The cosmetic compositions described herein may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:
  (i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.
  (ii) synthetic ethers containing from 10 to 40 carbon atoms;
  (iii) linear or branched hydrocarbons of mineral or synthetic origin, such as petroleum jelly, polydecenes, hydrogenated polyisobutene such as Parleam, and 4 0 squalane;
  (iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;
  (v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;
  (vi) higher fatty acids, such as oleic acid, linoleic acid or linolenic acid;
  (vii) carbonates, such as dicaprylyl carbonate, such as the product sold under the name Cetiol CO® by Cognis;
  (viii) fatty amides, such as isopropyl N-lauroyl sarcosinate, such as the product sold under the trade name Eldew SL 205® from Ajinomoto; and
  (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched C $C_8$-$C_{16}$ esters, and isohexyl neopentanoate.

Preferably, the oil is chosen from plant based or vegetable based oils, such as coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof.

Non-limiting examples of fatty compounds include:
  i. hydrocarbon oils of animal origin such as perhydrosqualene;
  ii. plant hydrocarbon oils, such as liquid triglycerides of fatty acids, for example sunflower oil, corn oil, soybean oil, marrow oil, grapeseed oil, sesame oil, hazelnut oil, apricot oil, macadamia oil, castor oil, avocado oil, caprylic/capric acid triglycerides;
  iii. oils of formula $R_9COOR_{10}$ in which $R_9$ represents a higher fatty acid residue containing from 7 to 19 carbon atoms and $R_{10}$ represents a branched hydrocarbon chain containing from 3 to 20 carbon atoms, such as, for example, Purcellin oil;
  iv. linear or branched hydrocarbons of mineral or synthetic origin, such as non-volatile liquid paraffins and derivatives thereof, petroleum jelly (petrolatum), polydecenes, and hydrogenated polyisobutene such as parleam, v. synthetic esters and ethers such as isopropyl myristate, octanoates, decanoates or ricinoleates of alcohols or of polyalcohols;
vi. fatty alcohols such as octyidodecanol or oleyl alcohol;
vii. partially hydrocarbonated and/or siliconated fluoro oils;
viii. silicone oils such as linear, non-volatile polydimethylsiloxanes (dimethicone) which are liquid or pasty at room temperature, phenyldimethicones, phenyltrimethicones and polymethylphenylsiloxanes; and mixtures thereof.

In some instances, the one or more fatty compounds may be selected form polyolefins (petrolatum), waxes, squalane, squalene, hydrogenated polyisobutene, hydrogenated polydecene, polybutene, mineral oil, pentahydrosqualene, dimethicone, and a mixture thereof.

Additional fatty compounds that are worth mentioning include fatty alcohols, fatty esters, fatty alcohols derivatives, fatty acid derivatives, such as those discussed below.

Fatty Alcohols

The one or more fatty compounds may be glycerolated and/or oxyalkylenated, include from 8 to 30 carbon atoms, and/or be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, cetyl alcohol, stearyl alcohol, isostearyl alcohol, oleyl alcohol, isotridecyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Fatty Esters

The fatty compounds of the skin tightening composition may be liquid or solid fatty esters at 25° C., 1 atm. The fatty esters may include esters from a $C_6$-$C_{32}$ fatty acid and/or a $C_6$-$C_{32}$ fatty alcohol. For example, the fatty compounds may include or be chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. These esters may be esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In one instance, the fatty compounds comprise one or more fatty acid monoesters. For the esters of monoalcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some instances, the fatty esters are cetyl esters, such as esters of saturated fatty acids and fatty alcohols. For example, the fatty esters may include or be chosen from cetyl palmitate, cetyl stearate, myristyl myristate, myristyl stearate, cetyl myristate, stearyl stearate, cetearyl ethylhexanoate, and mixtures thereof. In one instance, the fatty esters may be one or more of or chosen from isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof. In another instance, the fatty esters include or may be chosen from diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethyl hexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palm itate, 2-ethylhexyl palm itate, 2-hexyldecyl palm itate, 2-heptylundecyl palm itate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, cetearyl ethylhexanoate, and mixtures thereof. In yet a further instance, the skin-tightening composition includes one or more of or may have fatty compounds chosen from cetearyl alcohol, cetearyl ethylhexanoate, isopropyl myristate, and mixtures thereof.

Non-limiting examples of solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Non-limiting examples of liquid fatty acid include triglyceride oils of plant or synthetic origin, such as liquid fatty acid triglycerides containing 6 to 30 carbon atoms, for instance heptanoic or octanoic acid triglycerides, or alternatively, e.g., sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, shea butter oil, and mixtures thereof. In one instance, the one or more fatty compounds include at least one of or are selected from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof. In another instance, fatty compounds of the skin-tightening composition includes one or more fatty acid triglycerides, such as caprylic/capric triglyceride.

Fatty Alcohol Derivatives

The skin-tightening compositions may, in some instances, include fatty alcohol derivatives such as alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof. Liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Fatty Acid Derivatives

The skin-tightening compositions may, in some instances, include fatty acid derivatives. The fatty acid derivatives are defined herein to include fatty acid esters of the fatty alcohols as defined above, fatty acid esters of the fatty alcohol derivatives as discussed above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

Non-Ionic Surfactants(s)

The skin tightening composition may, optionally, include one or more nonionic surfactants. Although the skin tightening composition is typically an emulsion when containing one or more nonionic surfactants, the skin tightening composition may alternatively be anhydrous when containing such nonionic surfactants.

The nonionic surfactant(s) may include one or more of peg-30 dipolyhydroxystearate, polyglyceryl-4 diisostearate/polyhydroxystearate/sebacate, polyglyceryl-4 isostearate, polyglyceryl-2 dipolyhydroxystearate, dimethicone (and) peg/ppg-18/18 dimethicone, lauryl peg-9 polydimethylsiloxyethyl dimethicone, and a combination thereof. The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms. The number of ethylene oxide or propylene oxide groups of the foregoing compounds may range from 2 to 50, and the number of glycerol groups may range from 1 to 30. Mention may be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24)alkylpolyglycosides, N—(C6-C24)alkylglucamine derivatives, amine oxides such as (C10-C14)alkylamine oxides or N—(C10-C14)acylaminopropylmorpholine oxides; and mixtures thereof. Maltose derivatives may also be mentioned.

The nonionic surfactants may be chosen from polyoxyalkylenated or polyglycerolated nonionic surfactants. The oxyalkylene units are more preferably oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups—such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof. As glyceryl esters of fatty acids, glyceryl stearate (glyceryl mono-, di- and/or tristearate) (CTFA name: glyceryl stearate) or glyceryl ricinoleate and mixtures thereof can in particular be cited. As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited. Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Water-Soluble Solvents

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_1$-$C_{30}$, $C_1$-$C_{15}$, $C_1$-$C_{10}$, or $C_1$-$C_4$ alcohols), organic solvents, polyols (polyhydric alcohols), glycols (e.g., butylene glycol, caprylyl glycol, etc.), and a mixture thereof.

In some cases, the water-soluble solvent is a monoalcohol. Non-limiting examples of monoalcohols include ethanol, propanol, butanol, pentanol, hexanol, isopropyl alcohol, cyclohexanol, isobutyl alcohol, 2-methyl-2-butanol (2-methylbutan-2-ol), and a mixture thereof. In some instances, the monoalcohols comprise or are chosen from ethanol, propanol, butanol, pentanol, an isomer thereof, or a combination thereof. In further instances, the one or more monoalcohol(s) includes or consists of ethanol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The water-soluble solvents may be organic solvents that can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol, alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. The term "polyol" should be understood as meaning, within the meaning of the present disclosure, an organic molecule comprising at least two free hydroxyl groups. The polyols of the cosmetic composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Non-limiting examples of polyols that may, optionally, be included in the cosmetic composition include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol, glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof. The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol.

In some cases, the polyol comprises glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some cases, the cosmetic composition achieves the improved penetration of skin active agents into adult human skin. For example, the cosmetic compositions may achieve penetration of the skin active ingredient into the epidermis and dermis of skin. In some cases, the cosmetic composition may obtain about 2 µg/cm$^2$ or more, 2.1 µg/cm$^2$ or more, 2.2 µg/cm$^2$ or more, 2.3 µg/cm$^2$ or more, 2.4 µg/cm$^2$ or more, 2.5 µg/cm$^2$ or more, 2.6 µg/cm$^2$ or more, 2.7 µg/cm$^2$ or more, 2.8 µg/cm$^2$ or more, 2.9 µg/cm$^2$ or more, 3 µg/cm$^2$ or more of skin active agent in the epidermis and dermis of human skin. In certain embodiments, the cosmetic compositions obtain the improved penetration of skin active agents without the use of penetration enhancers.

Some therapeutic or cosmetic compositions achieve epidermal penetration by using a skin penetration enhancing carrier or vehicle. Such carrier or vehicles (which are compounds or mixtures of compounds) are often described as "penetration enhancers" or "skin enhancers." Typical penetration enhancers, which may be optionally excluded from the cosmetic composition, include sulphoxides (such as dimethylsulphoxide, DMSO), azones (e.g., laurocapram), pyrrolidones, (for example 2-pyrrolidone, 2P), alcohols and alkanols (ethanol, or decanol), surfactants (also common in dosage forms) and terpenes. Some penetration enhancers are capable of inserting between the hydrophobic tails of the bilayer, thus disturbing their packing, increasing their fluidity and, subsequently, leading to easier diffusion of lipid-like penetrants. The inventors surprisingly discovered that certain cosmetic compositions according to the disclosure provided improved penetration of skin active agents into adult human skin without necessitating the use of certain penetration enhancers. Nevertheless, in some cases, it may be desirable to include penetration enhancers, such as those discussed herein.

In some cases, the cosmetic composition has 5 wt. % or less, 4 wt. % or less, 3 wt. % or less, 2 wt. % or less, or 1 wt. % or less of any one of the foregoing penetration enhancers. In at least one instance, the cosmetic composition is free of or essentially free of any one of the foregoing penetration enhances. Additionally or alternatively, the cosmetic composition may have about 5 wt. % or less, 4 wt. % or less, 3 wt. % or less, 2 wt. % or less, or 1 wt. % or less of a total amount of penetration enhancers. For instance, the cosmetic composition may be free of or essentially free of penetration enhancers.

The cosmetic composition are generally formulated as an emulsion. Typically, the cosmetic compositions are formulated to be oil-in-water emulsions, with the fatty phase emulsified in the hydrophilic phase. However, in some instances, the cosmetic compositions may be formulated to have a hydrophilic phase (e.g., alcohols, glycols, polyols, etc.) emulsified in the fatty phase. The cosmetic composition may be formulated, in some cases, to be lotions, serums, creams, sprays or any other suitable form of product.

Additionally, the instant disclosure relates to methods of treating the skin comprising application of the cosmetic composition of the instant disclosure to the skin. The cosmetic compositions are additionally useful in methods for treating and/or repairing skin damage due to photoaging, and diminishing the appearance of wrinkles, dark spots, and uneven skin texture. The aforementioned methods may be non-therapeutic.

Suitable components, such as those listed below, may be included or excluded from the formulations for the cosmetic compositions depending on the specific combination of other components, the form of the cosmetic compositions, and/or the use of the formulation (e.g., a lotion, a serum, a gel, a cream, a spray, etc.).

Thickening Agents

In addition to the polymers of the rheological-modifying and stabilizing polymer blend, additional thickening agent may optionally be included in the cosmetic composition in order to adjust and/or achieve a desired viscosity. However, additional thickening agents are not required and may be excluded from the compositions. Non-limiting examples of thickening agents that may be included in the cosmetic compositions are set forth below.

Mineral Thickening Agents

Mineral thickening agents are mineral based compounds that thicken or modify the viscosity of the skin tightening compositions. Non-limiting examples of mineral thickening agents include silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite), and a mixture thereof.

In some instances, the skin tightening compositions may include one or more mineral thickening agents selected from optionally modified silicas, optionally modified clays, and a mixture thereof. The mineral thickening agents may be selected from optionally modified silicas, optionally modified clays, and a mixture thereof. In some instance, the mineral thickening agents are chosen from lipophilic (organophilic) clays, in particular modified hectorites; hydrophobic-treated fumed silica; hydrophobic silica aerogels, and mixtures thereof (e.g., disteardimonium hectorite, silica silylate, or a mixture thereof).

The mineral thickening agents may be selected from silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite).

Optionally Modified Silicas

Optionally modified silicas include fumed silica optionally subjected to a hydrophobic surface treatment, the particle size of which may be less than 1 µm. Specifically, it is possible to chemically modify the surface of the silica, by chemical reaction generating a reduced number of silanol groups present at the surface of the silica. Silanol groups can in particular be replaced by hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA (6th edition, 1995). They are sold, for example, under the references Aerosil R812 by the company Degussa, and Cab-O-Sil TS-53 by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972 and Aerosil R974 by the company Degussa, and Cab-O-Sil TS-610 and Cab-O-Sil TS-720 by the company Cabot.

The hydrophobic fumed silica in particular may have a particle size that is nanometric to micrometric, for example ranging from about 5 to 200 nm.

The optionally modified silicas may, for instance, be silica aerogel particles. Silica aerogels are porous materials obtained by replacing (by drying) the liquid component of a silica gel with air. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles may have a specific surface area per unit mass ($S_M$) ranging from 500 to 1500 $m^2/g$, preferably from 600 to 1200 $m^2/g$ and better still from 600 to 800 $m^2/g$, and a size expressed as the volume mean diameter (D[0.5]) ranging from 1 to 1500 µm, better still from 1 to 1000 µm, preferably from 1 to 100 µm, in particular from 1 to 30 µm, more preferably from 5 to 25 µm, better still from 5 to 20 µm, and even better still from 5 to 15 µm. In some instances, the hydrophobic silica aerogel particles have a size expressed as volume-mean diameter (D[0.5]) ranging from 1 to 30 µm, preferably from 5 to 25 µm, better still from 5 to 20 µm and even better still from 5 to 15 µm.

The hydrophobic silica aerogel particles may have a specific surface area per unit mass ($S_M$) ranging from 600 to 800 $m^2/g$ and a size expressed as the volume mean diameter (D[0.5]) ranging from 5 to 20 µm and even better still from 5 to 15 µm. The hydrophobic silica aerogel particles may have a specific surface area per unit of volume Sv ranging from 5 to 60 $m^2/cm^3$, preferably from 10 to 50 $m^2/cm^3$ and better still from 15 to 40 $m^2/cm^3$.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. In some instances, it is particularly useful to use hydrophobic silica aerogel particles surface-modified with trimethylsilyl groups. Mention may be made of the aerogels sold by the company Cabot under the references Aerogel TLD 201, Aerogel OGD 201, Aerogel TLD 203, Enova Aerogel MT 1100 and Enova Aerogel MT 1200. Particularly useful aerogels include hydrophobic silica aerogels, preferably of silyl silica (INCI name: silica silylate).

Optionally Modified Clays

Clays are silicates containing a cation that may be chosen from calcium, magnesium, aluminum, sodium, potassium and lithium cations, and mixtures thereof. Examples of such material include, but are not limited to clays of the smectite family, and also of the vermiculite, stevensite and chlorite families. These clays can be of natural or synthetic origin.

Mention may particularly be made of smectites, such as saponites, hectorites, montmorillonites, bentonites or beidellite and in particular synthetic hectorites (also known as laponites), such as the products sold by Rockwood Additives Limited under the names Laponite XLS, Laponite XLG, Laponite RD, Laponite RDS and Laponite XL21 (these products are sodium magnesium silicates and in particular sodium lithium magnesium silicates); bentonites, such as the product sold under the name Bentone HC by Rheox; magnesium aluminum silicates, which are in particular hydrated, such as the products sold by Vanderbilt Company under the name Veegum Ultra, Veegum HS or Veegum DGT, or also calcium silicates and in particular that in synthetic form sold by the company under the name Micro-Cel C.

In some instances, organophilic clays are preferred, more particularly modified clays, such as montmorillonite, bentonite, hectorite, attapulgite and sepiolite, and mixtures thereof. The clay may be optionally modified bentonite or an optionally modified hectorite. Clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made of hectorites modified with a quaternary amine, more specifically with a $C_{10}$ to $C_{22}$ fatty acid ammonium halide, such as a chloride, such as hectorite modified with distearyldimethylammonium chloride (CTFA name: Disteardimonium hectorite), for instance the product sold under the name Bentone 38V, Bentone 38V CG or Bentone EW CE by the company Elementis, or stearalkonium hectorites, such as Bentone 27 V. In some instances, the clay is preferably disteardimonium hectorite.

Mention may also be made of quaternium-18 bentonites, such as those sold under the names Bentone 34 by the company Elementis, Tixogel VP by the company United Catalyst and Claytone 40 by the company Southern Clay; stearalkonium bentonites, such as those sold under the names Tixogel LG by the company United Catalyst and Claytone AF and Claytone APA by the company Southern Clay; or quaternium-18/benzalkonium bentonites, such as that sold under the name Claytone HT by the company Southern Clay. In some instances, it is preferable that the clay is chosen from organophilic modified clays, in particular organophilic modified hectorites, in particular modified with distearyldimethylammonium chloride (CTFA name: Disteardimonium hectorite).

Non-Mineral Thickening Agents

Non-mineral thickening agents, if present, may be lipophilic or hydrophilic, i.e., they may be appropriate for thickening an oily phase or an anhydrous composition or they may be appropriate for thickening an aqueous phase or an aqueous composition. For anhydrous compositions, lipophilic thickening agents or thickening agents that thicken anhydrous (e.g., oily) compositions are useful. Similarly, for aqueous compositions, hydrophilic thickening agents are useful.

Non-limiting examples of the non-mineral thickening agents useful for thickening anhydrous compositions include $C_{12}$-$C_{22}$ alkyl acrylate/hydroxyethylacrylate copolymer (INTELIMER), ethylene diamine/stearyl dimer dilinoleate copolymer such as OLEOCRAFT LP-10-PA-(MV) sold by Croda, polyamide-8 such as OLEOCRAFT LP-20-PA-(MV) sold by Croda, poly $C_{10}$-$C_{30}$ alkyl acrylate such as INTELIMER IPA 13-6 or INTELIMER IPA 13-1 NG Polymer sold by Air Products & Chemicals, nylon-611/dimethicone copolymer such as Dow Corning 2-8179 Gellant sold by Dow Corning, or dextrin palmitate such as RHEOPEARL KL2-OR sold by Chiba Flour Milling.

Additional non-limiting examples of non-mineral thickening agents useful for thickening anhydrous compositions include thickening polymers such as block copolymers of styrene with isoprene, butadiene, ethylene/propylene or ethylene/butylene including those presently available under the trade name KRATON, and particularly hydrogenated styrene/isoprene linear diblock copolymers. A related category of thickening polymer comprises polymers of alpha methylstyrene and styrene, such as those under the trade name KRISTALEX. Yet another thickening polymer comprises alkyl substituted galactomannan available under the trade name N-HANCE AG. Non-mineral thickening agents useful for thickening anhydrous compositions may also include thickening polymers such as vinyl pyrrolidone with polyethylene containing at least 25 methylene units, such as triacontanyl polyvinylpyrrolidone, under the trade name Antaron WP-660.

Non-limiting examples of non-mineral thickening agents may, optionally, be included for thickening aqueous compositions include xanthan gum, guar gum, biosaccharide gum, cellulose, acacia Seneca gum, sclerotium gum, agarose, pechtin, gellan gum, hyaluronic acid. Additionally, the one or more non-mineral thickening agents may be polymeric thickening agents such as, for example, ammonium polyacryloyldimethyl taurate, ammonium acryloyldimethyl-taurateNP copolymer, sodium polyacrylate, acrylates copolymers, polyacrylamide, carbomer, and acrylates/C10-30 alkyl acrylate crosspolymer.

Additional, non-limiting examples of various types of non-mineral thickening agents include:
Carboxylic Acid Polymers These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickening agents useful herein are those selected from carbomers, acrylates/C10-C30 alkyl acrylate crosspolymers, and mixtures thereof.
Crosslinked Polyacrylate Polymers The compositions of the present disclosure can optionally contain crosslinked polyacrylate polymers useful as thickening agents or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078, 4,599,379 and EP 228, 868, which are all incorporated herein by reference in their entirety.
Polyacrylamide Polymers The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.
Polysaccharides A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™, provided by CS11 from Michel Mercier Products Inc.
Gums Other thickening and gelling agents useful herein include materials which are primarily derived from natural sources. Non-limiting examples of these thickening and/or gelling agent include gums such as those chosen from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The amount of thickening agent(s) in the compositions of the instant disclosure other than the polymers of the polymer blend can vary. In some instances, the compositions do not include thickening agent(s) other than the polymers of the polymer blend, i.e., the compositions may be free or essentially free of thickening agent(s) other than the polymers of the polymer blend. However, in some instances, the compositions may include about 0.01 to about 10 wt. % of thickening agent(s) other than the polymers of the polymer blend. Similarly, in some instances, the composition may include about 0.01 to about 6 wt. %, about 0.01 to about 5 wt. %, about 0.01 to about 4 wt. %, about 0.01 to about 2 wt. %, about 0.01 to about 1 wt. %, about 0.1 to about 10 wt. %, about 0.1 to about 6 wt. %, about 0.1 to about 5 wt. %, about 0.1 to about 4 wt. %, about 0.1 to about 2 wt. %, or 5 wt. % or less, 4 wt. % or less, 3 wt. % or less, 2 wt. %, 1 wt. % or less, 0.5 wt. % or less, or 0.1 wt. % or less of thickening agent(s) other than the polymers of the polymer blend.

Mattifying Agents(s)

The compositions of the instant disclosure may optionally include one or more mattifying agents. The amount of mattifying agents in the cosmetic composition may be, e.g., about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, based on the total weight of the composition.

Mattifying agents (also referred to as "mattifying fillers") refer to material that gives the complexion more transparency and a hazy effect and provides skin with a natural and desirable appearance, without conferring on it a greasy, gleaming and shiny appearance. To do this, these materials are often absorbent fillers such as talc, silica, kaolin or fillers having light scattering optical properties, which properties are known under the name "soft focus" effect. In addition to reducing the shine or oiliness, mattifying agents can contribute to the overall texture and thickness of a cosmetic composition. Mattifying agents are often (but not always) particulate material or powders.

Cosmetic compositions containing mattifying agents may be characterized by means of the following protocol. The test composition is spread out at a rate of 2 mg/cm$^2$ on a contrast card (Prufkarte type 24/5-250 cm$^2$ sold by the company Erichsen) using a mechanical film spreader. The composition is then dried overnight at a temperature of 37° C. prior to measurement of its reflection using a gonioreflectometer sold by the company Micromodule. The intensity reflected specularly at 30° (R) and scattered at 90° (D) are successively measured. The result obtained is the ratio R between the specular reflection and the diffuse reflection. The value of R is proportionately smaller the greater the mattifying effect afforded by the filler. A value of R of less than or equal to 2 generally indicates a mattifying effect. The mattifying agents according to the instant disclosure include those which, preferably at a content of 5% in a cosmetic composition, give a value of R of less than 1.5 and preferably less than 1.

Non-limiting examples of mattifying agents include: silicas, clays, silicate derivatives, hydrophobic silica aerogel particles, porous silica microparticles, for instance the Silica Beads SB150 and SB700 from Miyoshi with a mean size of 5 microns; the Sunsphere Series-H products from Asahi Glass, for instance Sunsphere H33, H51 and H53 with respective sizes of 3, 5 and 5 μm, polytetrafluoroethylene powders, for instance PTFE Ceridust 9205F from Clariant, with a mean size of 8 microns, silicone resin powders, for instance the silicone resin Tospearl 145A from GE Silicone, with a mean size of 4.5 microns, hollow hemispherical silicone particles, for instance NLK 500, NLK 506 and NLK 510 from Takemoto Oil and Fat, acrylic copolymer powders, especially of polymethyl(meth)acrylate, for instance the PMMA particles Jurymer MBI from Nihon Junyoki, with a mean size of 8 microns, the hollow PMMA spheres sold under the name Covabead LH 85 by the company Wackher, and the vinylidene chloride/acrylonitrile/methylene methacrylate expanded microspheres sold under the name Expancel; wax powders, for instance the paraffin wax particles MicroEase 114S from MicroPowders, with a mean size of 7 microns, polyethylene powders, especially comprising at least one ethylene/acrylic acid copolymer, and in particular consisting of ethylene/acrylic acid copolymers, for instance the Flobeads EA 209 particles from Sumitomo (with a mean size of 10 microns), crosslinked elastomeric organopolysiloxane powders coated with silicone resin, especially with silsesquioxane resin, as described, for example, in patent U.S. Pat. No. 5,538,793. Such elastomeric powders are sold under the names KSP-100, KSP-101, KSP-102, KSP-103, KSP-104 and KSP-105 by the company Shin-Etsu, polyamide (Nylon) powders, for instance Nylon 12 particles of the Orgasol type from Atofina, with a mean size of 10 microns, powders of polymethyl methacrylate (PMMA)

type, talc, silica/TiO$_2$ or silica/zinc oxide composites, styrene/acrylic copolymer powders, and mixtures thereof.

Among clays, mention may be made of clays of the smectite family, such as laponite, of the kaolinite family, such as kaolinite, dickite or nacrite, optionally modified clays of the halloysite, dombassite, antigorite, benthierine or pyrophyllite family, montmorillonites, beidellite, vermiculites, talc, stevensite, hectorites, saponites, chlorites, sepiolite and illite. Note that certain clays may also be categorized as thickening agents.

Clays include products that are described, for example, in the publication Mineralogie des argiles [Mineralogy of Clays], S. Caillere, S. Henin, M. Rautureau, 2nd Edition 1982, Masson, which is incorporated herein by reference in its entirety. Natural clay is a sedimentary rock in large part composed of specific minerals, silicates, generally, of aluminum. Kaolin is a natural clay. The clays may also be synthetic. Clays can also be chemically modified by various compounds, such as acrylic acids, polysaccharides (for example carboxymethylcellulose) or organic cations. In some instances, the cosmetic compositions of the instant disclosure include a clay selected from the group consisting of kaolinite, montmorillonites, saponites, laponites, hectorites (including disteardimonium hectorite), and illites.

Silica derivatives that may be mentioned include silica powders, for instance the porous silica microspheres sold under the name SILICA BEADS SB-700 sold by the company Miyoshi, the products SUNSPHERE H51, SUNSPHERE H33 and SUNSPHERE H53 sold by the company Asahi Glass; the polydimethylsiloxane-coated amorphous silica microspheres sold under the name SA SUNSPHERE H-33 and SA SUNSPHERE H-53 sold by the company Asahi Glass; silica microbeads such as those sold under the name SB150 by the company Miyoshi.

In some instances, the cosmetic compositions include one or more mattifying agents selected from the group consisting of methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, clays (such as hectorite clays including distearidimonium hectorite), silicas, polymethysilsequioxane, and a mixture thereof. Preferably, the mattifying agent, if present, is aluminum starch octenylsuccinate.

Skin Active Agents(s)

The cosmetic compositions may, optionally, include one or more skin active agents, such as anti-aging agent, anti-wrinkle actives, antioxidants, humectants, moisturizing ingredients, depigmenting agents, and/or agents for treating oily skin etc. The skin active agents may be included in the cosmetic composition in an amount ranging from greater than zero to about to about 10 wt. %, based on the total weight of the composition. For example, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; from about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.05 to about 10 wt. %, about 0.05 to about 5 wt. %, about 0.05 to about 2.5 wt. %, about 0.05 to about 1 wt. %, about 0.05 to about 0.5 wt. %; about 0.1 to about 10 wt. %, about 0.1 to about 5 wt. %, about 0.1 to about 2.5 wt. %, about 0.1 to about 1 wt. %, about 0.1 to about 0.5 wt. %; from about 1 to about 10 wt. %, about 1 to about 8 wt. %, about 1 to about 6 wt. %, about 1 to about 5 wt. %, about 1 to about 4 wt. %, about 1 to about 3 wt. %; from about 2 to about 10 wt. %, about 2 to about 8 wt. %, about 2 to about 6 wt. %, about 2 to about 5 wt. %, about 2 to about 4 wt. %; from about 3 to about 10 wt. %, about 3 to about 8 wt. %, about 3 to about 6 wt. %, about 3 to about 5 wt. %; from about 4 to about 10 wt. %, about 4 to about 8 wt. %, about 4 to about 6 wt. %, including ranges and subranges therebetween, based on the total weight of the cosmetic composition.

A non-limiting discussion of skin active agents that may, in some cases, be included in the cosmetic composition is provided below:

Humectants and/or Moisturizing Ingredients

Examples of humectants and/or moisturizing ingredients include glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting Agents

Depigmenting agents that may be incorporated in the cosmetic composition include those chosen from alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Active

The cosmetic composition may include one or more anti-wrinkle actives. The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids (such as, retinol palmitate and retinol), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of Dioscorea plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the cosmetic composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N6-phenethyladenosine, 2-p-(2-carboxyethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

Skin Active Agent for Oily Skin

The cosmetic composition may, optionally, include a skin active agent that addresses oily skin. These agents can be sebo-regulating or antiseborrhoeic agents capable of regulating the activity of sebaceous glands. Exemplary skin active agents for addressing oily skin include: retinoic acid, retinol, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of *Terminalia chebula, nasturtium* and of bioavailable zinc (microalgae), such as that sold under the name Seborilys Green Tech;—extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed laminaria extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of Sophora angustifolia, such as those sold under the name Sophora powder or Sophora extract by Bioland—extracts of cinchona bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Antioxidants

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (Myrciaria dubia), acerola, emblica officinalis, and bioflavonoids from rose hip and citrus may be used including watersoluble bioflavonoids such as hesperidin methyl chalcone may also be used.

Sesame (Sesamum indicum) or sesame lignan may also be added. Sesame and its lignans (the fibrous compounds associated with the sesame) act as antioxidants. Sesame seed lignans significantly enhance vitamin E activity.

Other antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ-tocotrienol, d-delta-tocotrienol,) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewers grain or oats. As used herein, the term "tocotrienols" includes tocotrienol-rich-fractions obtained from these natural products as well as the pure compounds. The increased glutathione peroxidase activity protects the skin from oxidative damage.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids

The active agent may be an antioxidant selected from the group of flavonoids. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, lcariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of Curcuma longa. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (Sesamum indicum) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

C-Glycoside(s)

The cosmetic compositions may include a C-glycoside, for instance, as a skin active ingredient. For example, a C-glycoside in an amount of about 0.1 to about 10 wt. %, based on the total weight of the cosmetic composition. For example, the amount of C-glycoside present in the cosmetic composition may be from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %; about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %; about 3 to about 10 wt. %, about 3 to about 9 wt. %, about 3 to about 8 wt. %, about 3 to about 7 wt. %, about 3 to about 6 wt. %, about 3 to about 5 wt. %, or about 3 to about 4 wt. %, based on the total weight of the cosmetic composition.

The cosmetic composition may include one or more C-glycoside(s) having a structure in accordance with general formula (I):

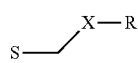

(I)

in which:
R represents a saturated $C_1$ to $C_{10}$, in particular $C_1$ to $C_4$, alkyl radical which can optionally be substituted by at least one radical chosen from OH, COOH or COOR"$_2$, with R"$_2$ being a saturated $C_1$-$C_4$ alkyl radical,
S represents a monosaccharide or a polysaccharide comprising up to 20 sugar units, in particular up to 6 sugar units, in pyranose and/or furanose form and of the L and/or D series, it being possible for the said monosaccharide or polysaccharide to be substituted by a hydroxyl group which is necessarily free and optionally one or more optionally protected amine functional group(s), and
X represents a radical chosen from the —CO—, —CH(OH)—, —CH(NH$_2$)—, —CH(NHCH$_2$CH$_2$CH$_2$OH)—, —CH(NHPh)- and —CH(CH$_3$)—groups and in particular a —CO—, —CH(OH)—or —CH(NH$_2$)—radical and more particularly a —CH(OH)—radical,
wherein the S—CH2-X bond represents a bond of C-anomeric nature, which can be α or β, and also their physiologically acceptable salts, their solvates, such as the hydrates, and their optical and geometrical isomers.

The C-glycosides of formula (I) preferably have a structure, wherein R denotes a saturated linear $C_1$ to $C_6$, in particular $C_1$ to $C_4$, preferentially $C_1$ to $C_2$, alkyl radical and more preferably a methyl radical. Mention may, in particular, be made of the following alkyl groups for the C-glycosides (such as R): methyl, ethyl, isopropyl, n-propyl, n-butyl, t-butyl, isobutyl, sec-butyl, pentyl, n-hexyl, cyclopropyl, cyclopentyl and cyclohexyl groups.

According to at least one embodiment, use may be made of a C-glycoside compound corresponding to the formula (I) for which S represents a monosaccharide or a polysaccharide comprising up to 6 sugar units, such as in pyranose and/or furanose form and of L and/or D chimeric series. The mono- or polysaccharide exhibits at least one free hydroxyl functional group and/or optionally one or more protected amine functional groups, where X and R otherwise retain all of the definitions given above.

Advantageously, a monosaccharide of the invention can be chosen from D-glucose, D-galactose, D-mannose, D-xylose, D-lyxose or L-fucose, L-arabinose, L-rhamnose, D-glucuronic acid, D-galacturonic acid, D-iduronic acid, N-acetyl-D-glucosamine or N-acetyl-D-galactosamine and advantageously denotes D-glucose, D-xylose, N-acetyl-D-glucosamine, L-fucose, and a mixture thereof. In one instance, the monosaccharide is D-xylose.

More particularly, a polysaccharide of the invention comprising up to 6 sugar units can be chosen from D-maltose, D-lactose, D-cellobiose, D-maltotriose, a disaccharide combining an uronic acid chosen from D-iduronic acid or D-glucuronic acid with a hexosamine chosen from D-galactosamine, D-glucosamine, N-acetyl-D-galactosamine or N-acetyl-D-glucosamine, an oligosaccharide comprising at least one xylose that can advantageously be chosen from xylobiose, methyl-β-xylobioside, xylotriose, xylotetraose, xylopentaose, xylohexaose and a mixture thereof. Preferably, the oligosaccharide is xylobiose, which is composed of two xylose molecules linked via a 1-4 bond. More particularly, S can represent a monosaccharide chosen from D-glucose, D-xylose, L-fucose, D-galactose, D-maltose, and a mixture thereof. In some cases, the monosaccharide is D-xylose.

Preferably, the C-glycoside may be a derivative of formula (I) for which:
R denotes an unsubstituted linear $C_1$-$C_4$, in particular $C_1$-$C_2$, alkyl radical, especially a methyl radical;
S represents a monosaccharide as described above and chosen in particular from D-glucose, D-xylose, N-acetyl-D-glucosamine or L-fucose, and in particular D-xylose; and
X represents a group chosen from —CO—, —CH(OH)— or —CH(NH$_2$)—and preferably a —CH(OH)—group.

The compounds described herein may be in the form of a salt. Acceptable salts of the compounds described in the present disclosure comprise conventional non-toxic salts of the said compounds, such as those formed from organic or inorganic acids. Mention may be made, by way of example, of the salts of inorganic acids, such as sulfuric acid or hydrochloric acid. Mention may also be made of the salts of organic acids, which can comprise one or more carboxylic, sulfonic or phosphonic acid groups. Mention may in particular be made of propionic acid, acetic acid, terephthalic acid, citric acid and tartaric acid.

When the compound of formula (I) comprises an acid group, neutralization of the acid group(s) can be carried out with an inorganic base, such as LiOH, NaOH, KOH, Ca(OH)$_2$, NH$_4$OH, Mg(OH)$_2$ or Zn(OH)$_2$, or with an organic base, such as a primary, secondary or tertiary alkylamine. For example, the compound of formula (I) may be neutralized with triethylamine or butylamine. This primary, secondary or tertiary alkylamine can comprise one or more nitrogen and/or oxygen atoms and can comprise, e.g., one or more alcohol functional groups. Mention may be made of 2-amino-2-methylpropanol, triethanolamine, 2-(dimethylamino)propanol or 2-amino-2-(hydroxymethyl)-1,3-propanediol. Mention may also be made of lysine or 3-(dimethylamino)propylamine.

Non-limiting examples of solvates which may be used in the cosmetic composition include conventional solvates, such as those formed during the final stage of preparation of said compounds due to the presence of solvents. Mention may be made, by way of example, of the solvates due to the presence of water or of linear or branched alcohols, such as ethanol or isopropanol. Of course, according to the disclsoure, a C-glycoside derivative corresponding to the formula (I) can be used alone or as a mixture with other C-glycoside derivatives and in any proportion.

A C-glycoside derivative which is suitable for the invention can in particular be obtained by the synthetic method described in the document WO 02/051828, which is incorporated herein in its entirety for all purposes.

Non-limiting examples of C-glycoside compounds which may be suitable for the cosmetic composition include:
C-β-D-xylopyranoside-n-propane-2-one,
C-α-D-xylopyranoside-n-propan-2-one,
C-β-D-xylopyranoside-2-hydroxypropane,
C-α-D-xylopyranoside-2-hydroxypropane,
1-(C-β-D-fucopyranoside)propan-2-one,
1-(C-α-D-fucopyranoside)propan-2-one,
1-(C-β-L-fucopyranoside)propan-2-one,
1-(C-α-L-fucopyranoside)propan-2-one,
1-(C-β-D-fucopyranoside)-2-hydroxypropane,
1-(C-α-D-fucopyranoside)-2-hydroxypropane,
1-(C-β-L-fucopyranoside)-2-hydroxypropane,
1-(C-α-L-fucopyranoside)-2-hydroxypropane,
1-(C-β-D-glucopyranosyl)-2-hydroxypropane,
1-(C-α-D-glucopyranosyl)-2-hydroxypropane,
1-(C-β-D-galactopyranosyl)-2-hydroxypropane,
1-(C-α-D-galactopyranosyl)-2-hydroxypropane,
1-(C-β-D-fucofuranosyl)propan-2-one,
1-(C-α-D-fucofuranosyl)propan-2-one,
1-(C-β-L-fucofuranosyl)propan-2-one,
1-(C-α-L-fucofuranosyl)propan-2-one,
C-β-D-maltopyranoside-n-propane-2-one,
C-α-D-maltopyranoside-n-propan-2-one,
C-β-D-maltopyranoside-2-hydroxypropane,
C-α-D-maltopyranoside-2-hydroxypropane, isomers therof, and/or mixtures thereof.

The cosmetic composition may, preferably, include a C-glycoside chosen from C-β-D-xylopyranoside-2-hydroxypropane, C-α-D-xylopyranoside-2-hydroxypropane, and a mixture thereof. In some cases, the C-glycoside is C-β-D-xylopyranoside-2-hydroxypropane. According to at least one embodiment, the C-glycoside compound can be C-β-D-xylopyranoside-2-hydroxypropane (or hydroxypropyl tetrahydropyran-triol), which may be provided in the form of a solution containing 30% by weight of active material in a water/propylene glycol (60/40% by weight) mixture.

pH Adjuster(s)

The cosmetic composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The cosmetic composition may include one or more bases, such as sodium hydroxide, potassium hydroxide and the like, to decrease the pH of the cosmetic composition. Additional or alternative acids and bases that are suitable for adjusting the pH of the cosmetic composition are readily known to one of ordinary skill in the art.

The amount of the pH adjuster in the cosmetic composition may be based on the desired pH of the final cosmetic composition and/or product. For example, the total amount of the pH adjuster may range from about 0.05 to about 20 wt. %, based on the total weight of the composition. In some instances, the total amount of pH adjuster is from about 0.05 to about 15 wt. %, about 0.5 to about 10 wt. %, about 1 to about 5 wt. %, about 1.5 to about 4 wt. %, or about 2.0 to about 3 wt. %, including ranges and sub-ranges therebetween, based on the total weight of the composition.

Miscellaneous Components

The compositions described herein may optionally include one or more miscellaneous components. Examples include, but are not limited to proteins, hydrolyzed proteins, amino acids, humectants and moisturizing agents, vitamins, fillers, structuring agents, propellants, shine agents, conditioning agents, antioxidants, penetrants, sequestrants, fragrances, buffers, dispersants, ceramides, preservatives, colorants, UV screening agents, vegetal extracts, and plasticizers. In some instances, the miscellaneous components are chosen from preservatives, fragrances, colorants, UV screening agents, antioxidants, vitamins, and mixtures thereof.

The total amount of miscellaneous components in the compositions of the instant disclosure may vary. In some instances, the amount of miscellaneous components is from about 0.01 to about 20 wt. %, based on the total weight of the cosmetic composition. Moreover, the total amount of the miscellaneous components may be from about 0.01 to about 10 wt. %, about 0.01 to about 5 wt. %, about 0.01 to about 2 wt. %, about 0.1 to about 10 wt. %, about 0.1 to about 5 wt. %, about 0.1 to about 2 wt. %, or 10 wt. % or less, 8 wt. % or less, 6 wt. % or less, 5 wt. % or less, 4 wt. % or less, 2 wt. % or less, 1 wt. % or less, 0.5 wt. % or less, or 0.1 wt. % or less, based on the total weight of the composition.

Methods of Use

The instant disclosure also relates to methods of using the polymer blends and the compositions described herein. For example, the cosmetic compositions can be used in a method that comprises applying the cosmetic compositions to the skin of humans. In some cases, the composition is applied to the face. Furthermore, the cosmetic composition can be used in methods for treating and/or repairing damage to skin (for example, damage from photoaging), and for diminishing the appearance of wrinkles, dark spots, and uneven skin texture of skin. The aforementioned methods may be non-therapeutic.

The cosmetic composition may be applied once per day, twice per day, or more than once or twice per day. In some cases, the composition is applied in the evenings before bed. In other cases, the compositions are applied in the morning. In still other cases, the composition may be applied immediately after washing the skin. The compositions may be used once, or for a series of days, weeks, or months. For example, the compositions may be used daily or twice daily for a period of 1, 2, 3, 4, 5, 6, 7, 8 or more weeks, or months.

In some instances, the cosmetic composition of the instant disclosure comprises:
- (a)(i) 0.1 to 8 wt. %, preferably 0.2 to 5 wt. %, more preferably 0.2 to 3 wt. % of a carbomer;
- (a)(ii) 0.1 to 5 wt. %, preferably 0.1 to 2 wt. %, more preferably 0.1 to 1 wt. % of acrylates/C10-30 alkyl acrylate crosspolymer;
- (a)(iii) 0.1 to 5 wt. %, preferably 0.1 to 2 wt. %, more preferably 0.1 to 1 wt. % of ammonium acryloyldimethyltaurate/steareth-25 methacrylate crosspolymer;
- (b) 60 to 90 wt. % of water;
- (c) optionally, one or more fatty compounds, for example, from 1 to 40 wt. %, preferably 1 to 25 wt. %, more preferably 5 to 20 wt. % of one or more fatty compounds, preferably one or more non-silicone fatty compounds;
- (d) optionally, one or more emulsifiers, for example from 0.1 to 10 wt. %, preferably 0.1 to 6 wt. %, more preferably 0.1 to 5 wt. % of one or more emulsifiers, preferably one or more emulsifiers chosen from glyceryl esters and derivatives, alkoxylated carboxylic acids (PEG-30 dipolyhydroxystearate), oxyalkylenated fatty acid esters of glycerol, oxyalkylenated fatty acid esters of sorbitan, oxyalkylenated fatty acid esters, oxyalkylenated fatty alkyl ethers, sugar esters (arachidyl glucoside), and mixtures thereof;
- (e) 1 to 40 wt. %, preferably 1 to 30 wt. %, more preferably 5 to 20 wt. % of one or more water-soluble solvents, for example, one or more water-soluble solvents chosen from a glycol, glycerin, a $C_1$-$C_4$ alcohol, a polyhydric alcohol, and a mixture thereof;
- (f) one or more skin active agents, preferably one or more skin active agents chosen from anti-aging agents, depigmenting agents, anti-wrinkle agents, agent that treat oily skin, mattifying agents, anti-oxidants, vitamins, anti-acne agents, anti-inflammatory agents, and electrolytes, more preferably, one or more skin active agents chosen from a C-glycoside derivative (hydroxypropyl tetrahydropyrantriol), a hyaluronic acid (sodium hyaluronate), salicylic acid (caproyl salicylic acid), an ester thereof, or a salt thereof;
- (g) optionally, one or more thickening agents other than components (a)(i), (a)(ii), and (a)(iii), for example, in an amount of 0.01 to 5, preferably 0.01 to 3, more preferably 0.01 to 2, even more preferably 0.1 to 5, and even more preferably 0.1 to 3 wt. %, for example one or more gums;
- (h) optionally, one or more miscellaneous ingredients, for example from about 0.01 to about 15 wt. %, about 0.01 to about 10, wt. % about 0.01 to about 5 wt. %, about 0.01 to 2 wt. %, about 0.1 to 10 wt. %, 0.1 to 5 wt. %, or 0.1 to 3 wt. %, for example, one or more preservatives, one or more pH adjusters (e.g., sodium and/or potassium hydroxide), one or more fragrances, one or more salts, one or more colorants and/or dyes, one or more preservatives (e.g., chlorphenesin and/or phenoxyethanol);

wherein
the composition has a pH of 5 to 9, preferably 5.5 to 7;
the weight ratio of (a)(i) to ((a)(ii)+((a)(iii)) is 0.5:1 to 2:1, preferably 0.7:1 to 1.5:1, more preferably from 0.8:1 to 1.2:1, even more preferably about 1:1;
all weight percentages are based on the total weight of the cosmetic composition.

The composition may be in the form of a gel, an emulsion (preferably an oil-in-water emulsion), a cream, a paste, or a lotion. Depending on the form of the composition, the viscosity can vary. Nonetheless, in some instances, the viscosity is from 5,000 cP to about 100,000 cP at 25° C. In some instances, the viscosity of the cosmetic compositions may be from about 5,000 cP to about 80,000 cP, about 5,000 cP to about 50,000 cP, about 5,000 cP to about 25,000 cP, about 5,000 cP to about 10,000 cP, 10,000 cP to about 100,000 cP, about 25,000 cP to about 100,000 cP, about 50,000 to about 100,000 cP, about 75,000 cP to about 100,000 cP, about 10,000 cP to about 90,000 cP, about 25,000 cP to about 75,000 cP, or about 30,000 cP to about 60,000 cP at 25° C.

The composition may be free or essentially free of cross-linked siloxane elastomers. Furthermore, the composition may be free or essentially free of silicones.

The composition may optionally include one or more thickening agents, which is separate from the carbomer, the acrylates/C10-30 alkyl acrylate crosspolymer, and the ammonium acryloyldimethyltaurate/steareth-25 methacrylate crosspolymer. For example, the thickening agent may be chosen from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

In some instances, the cosmetic composition of the instant disclosure comprises:
- (a)(i) 0.1 to 8 wt. %, preferably 0.2 to 5 wt. %, more preferably 0.2 to 3 wt. % of a carbomer;
- (a)(ii) 0.1 to 5 wt. %, preferably 0.1 to 2 wt. %, more preferably 0.1 to 1 wt. % of acrylates/C10-30 alkyl acrylate crosspolymer;
- (a)(iii) 0.1 to 5 wt. %, preferably 0.1 to 2 wt. %, more preferably 0.1 to 1 wt. % of ammonium acryloyldimethyltaurate/steareth-25 methacrylate crosspolymer;
- (b) 50 to 90 wt. %, preferably 55 to 85 wt. %, more preferably 60 to 80 wt. % of water;
- (c) optionally, one or more fatty compounds, for example, from 1 to 40 wt. %, preferably 1 to 25 wt. %, more preferably 5 to 20 wt. % of one or more fatty compounds, preferably one or more non-silicone fatty compounds, more preferably, one or more fatty compounds chosen from fatty alcohols (e.g., arachidyl alcohol, behenyl alcohol, cetearyl alcohol, triglycerides (e.g., caprylic/capric triglyceride), fatty esters (e.g., isononyl isononanoate and cetyl ethylhexanoate);
(d) optionally, one or more emulsifiers, for example from 0.1 to 10 wt. %, preferably 0.1 to 6 wt. %, more preferably 0.1 to 5 wt. % of one or more emulsifiers, preferably one or more emulsifiers chosen from glyceryl esters and derivatives, alkoxylated carboxylic acids (PEG-30 dipolyhydroxystearate), oxyalkylenated fatty acid esters of glycerol, oxyalkylenated fatty acid esters of sorbitan, oxyalkylenated fatty acid esters, oxyalkylenated fatty alkyl ethers, sugar esters (arachidyl glucoside), and mixtures thereof;
(e) 1 to 40 wt. %, preferably 1 to 30 wt. %, more preferably 5 to 20 wt. % of one or more water-soluble solvents, for example, one or more water-soluble solvents chosen from a glycol, glycerin, a $C_1$-$C_4$ alcohol, a polyhydric alcohol, and a mixture thereof, more preferably glycerin, propylene glycol, butylene glycol, or a mixture thereof; and
(f) one or more skin active agents, preferably one or more skin active agents chosen from anti-aging agents, depigmenting agents, anti-wrinkle agents, agent that treat oily skin, mattifying agents, anti-oxidants, vitamins, anti-acne agents, anti-inflammatory agents, and electrolytes, more preferably, one or more skin active agents chosen from a C-glycoside derivative (hydroxypropyl tetrahydropyrantriol), a hyaluronic acid (sodium hyaluronate), salicylic acid (capryloyl salicylic acid), an ester thereof, or a salt thereof; and
(g) optionally, one or more thickening agents other than components (a)(i), (a)(ii), and (a)(iii), for example, in an amount of 0.01 to 5, preferably 0.01 to 3, more preferably 0.01 to 2, even more preferably 0.1 to 5, and even more preferably 0.1 to 3 wt. %, for example one or more gums;
(h) optionally, one or more miscellaneous ingredients, for example from about 0.01 to about 15 wt. %, about 0.01 to about 10, wt. % about 0.01 to about 5 wt. %, about 0.01 to 2 wt. %, about 0.1 to 10 wt. %, 0.1 to 5 wt. %, or 0.1 to 3 wt. %, for example, one or more preservatives, one or more pH adjusters (e.g., sodium and/or potassium hydroxide), one or more fragrances, one or more salts, one or more colorants and/or dyes, one or more preservatives (e.g., chlorphenesin and/or phenoxyethanol);

wherein
the composition has a pH of 5 to 9, preferably 5.5 to 7;
the weight ratio of (a)(i) to ((a)(ii)+((a)(iii)) is 0.5:1 to 2:1, preferably 0.7:1 to 1.5:1, more preferably from 0.8:1 to 1.2:1, even more preferably about 1:1;
all weight percentages are based on the total weight of the cosmetic composition.

The composition may be in the form of a gel, an emulsion (preferably an oil-in-water emulsion), a cream, a paste, or a lotion. Depending on the form of the composition, the viscosity can vary. Nonetheless, in some instances, the viscosity is from 5,000 cP to about 100,000 cP. In some instances, the viscosity of the cosmetic compositions may be from about 5,000 cP to about 80,000 cP, about 5,000 cP to about 50,000 cP, about 5,000 cP to about 25,000 cP, about 5,000 cP to about 10,000 cP, 10,000 cP to about 100,000 cP, about 25,000 cP to about 100,000 cP, about 50,000 cP to about 100,000 cP, about 75,000 cP to about 100,000 cP, about 10,000 cP to about 90,000 cP, about 25,000 cP to about 75,000 cP, or about 30,000 cP to about 60,000 cP at 25° C.

The composition may be free or essentially free of cross-linked siloxane elastomers. Furthermore, the composition may be free or essentially free of silicones.

The composition may optionally include a thickening agent, which is separate from the carbomer, the acrylates/C10-30 alkyl acrylate crosspolymer, and the ammonium acryloyldimethyltaurate/steareth-25 methacrylate crosspolymer. For example, the thickening agent may be chosen from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

EXAMPLES

The following examples are provided primary for the purpose of elucidating the benefits achieved by embodiments of the disclosure. The examples serve to illustrate the technology without necessarily being limiting in nature.

Example 1

|  |  | Skin Cream | A wt. % |
|---|---|---|---|
| (a)(i) | Rheological- | CARBOMER (POLY(ACRYLIC ACID))[1] | 0.50 |
| (a)(ii) | Modifying and Stabilizing | ACRYLATES/C10-30 ALKYL ACRYLATE CROSSPOLYMER[2] | 0.23 |
| (a)(iii) | Polymer Blend | AMMONIUM ACRYLOYLDIMETHYLTAURATE/ STEARETH-25 METHACRYLATE CROSSPOLYMER[3] | 0.25 |
| (c) | Fatty Compounds | ARACHIDYL ALCOHOL, BEHENYL ALCOHOL, CETEARYL ALCOHOL, CAPRYLIC/CAPRIC TRIGLYCERIDE, ISONONYL ISONONANOATE, AND/OR CETYL ETHYLHEXANOATE | 8.13 |
| (d) | Emulsifiers/ Surfactants | CETEARYL GLUCOSIDE, TRIDECETH-6, PEG-30 DIPOLYHYDROXYSTEARATE, AND/OR ARACHIDYL GLUCOSIDE | 0.41 |
| (e) | Water-Soluble Solvents | GLYCERIN, PROPYLENE GLYCOL, AND/OR BLUTYLENE GLYCOL | 14.25 |

|     |                 | Skin Cream                                                                                                         | A wt. % |
| --- | --------------- | ------------------------------------------------------------------------------------------------------------------ | ------- |
| (f) | Skin Active     | HYDROXYPROPYL TETRAHYDROPYRANTRIOL[4]                                                                              | 3.15    |
|     |                 | SODIUM HYALURONATE, CAPRYLOYL SALICYLIC ACID (LHA), ADENOSINE, AND/OR TRISODIUM ETHYLENEDIAMINE DISUCCINATE         | 1.00    |
| (g) | Thickening Agent | HYDROXYPROPYL GUAR                                                                                                | 0.08    |
| (h) | pH Adjuster     | SODIUM HYDROXIDE                                                                                                   | 0.23    |
|     | Preservatives   | CHLORPHENESIN AND/OR PHENOXYETHANOL                                                                                | 0.80    |
| (b) | Water           | WATER                                                                                                              | QS 100  |

[1]Provided from SYNTHALEN K produced by (3 V)
[2]Provided from CARBOPOL ULTREZ-21 (Lubrizol)
[3]Provided from ARISTOFLEX HMS (Clariant)
[4]Provided from PRO-XYLANE (PX) (L'Oréal) (a sugar-protein hybrid made from xylose)

The term "blend" (for example, in the phrase "polymer blend") is used throughout the instant disclosure. The term does not indicate that the components of the blend must be first combined with each other before the components are added into a composition. In other words, each component of a "blend" can individually be added into a composition or each component of a "blend" can be combined with other components of the "blend" and then together added into a composition.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the cosmetic compositions of the instant disclosure can be free or essentially free of all components and elements positively recited throughout the instant disclosure.

In some instances, the cosmetic compositions of the present disclosure may be substantially free of non-incidental amounts of the ingredient(s) or compound(s) described herein. A non-incidental amount of an ingredient or compound is the amount of that ingredient or compound that is added into the cosmetic composition by itself. For example, a cosmetic composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the composition includes both components (or the composition includes more than two components that overlap), an overlapping compound does not represent more than one component. For example, tocopherol may be characterized as both a skin active agent and a preservative. If a particular composition includes both a skin active agent and a preservative, tocopherol would serve only as the skin active agent or only as the preservative (tocopherol does not simultaneously serve as both the skin active agent and preservative).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense. In all instances throughout the instant disclosure the term "comprising" may be changed to "consisting of" or "consisting essentially of" to more narrowly identify what is included in the blends, compositions, and methods described herein, i.e., to limited what is included in the blends, compositions, and methods of the instant disclosure to the elements and/or steps specifically recited.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements chosen from A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein with respect to cosmetic compositions refers to the application of the compositions of the present disclosure onto the surface of keratinous substrates such as the skin or hair of a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt.

%, less than about 0.1 wt. %, or none of the specified material. All components set forth herein may be optionally included or excluded from the compositions/method/kits. When excluded, the compositions/methods/kits may be free or essentially free of the component. For example, a particular composition may be free or essentially free of silicones and/or free or essentially free of crosslinked siloxane elastomers.

What is claimed is:

1. A cosmetic composition comprising:
   (a) a rheological-modifying and stabilizing polymer blend comprising:
      (i) about 40 to 60 wt. % of a carbomer;
      (ii) about 22 to 28 wt. % of an acrylates/C10-30 alkyl acrylate crosspolymer; and
      (iii) about 22 to 28 wt. % of an ammonium acryloyldimethyltaurate/steareth-25 methacrylate crosspolymer; and
   (b) water;
      wherein all weight percentages are based on the total weight of the polymer blend; and wherein (i) and ((ii)+(iii)) are in a weight ratio of 0.5:1 to 2:1 ((i):((ii)+(iii))).

2. The cosmetic composition of claim 1, wherein (i) and ((ii)+(iii)) are in a weight ratio of 0.8:1 to 1.3:1 0.5:1 to 2:1 ((i):((ii)+(iii))) the weight ratio of (i) to ((ii)+(iii)) is 0.5:1 to 2:1.

3. The cosmetic composition of claim 1 comprising 0.1 to 10 wt. % of the polymer blend.

4. The cosmetic composition of claim 1 comprising:
   (a)(i) 0.1 to 8 wt. % of the carbomer;
   (a)(ii) 0.1 to 5 wt. % of the acrylates/C10-30 alkyl acrylate crosspolymer;
   (a)(iii) 0.1 to 5 wt. % of the ammonium acryloyldimethyltaurate/steareth-25 methacrylate crosspolymer; and
   (b) 60 to 90 wt. % of the water;
   wherein all weight percentages are based on the total weight of the cosmetic composition.

5. The composition of claim 4, wherein (a)(i) and ((a)(ii)+(a)(iii)) are in a weight ratio of 0.8:1 to 1.3:1 0.5:1 to 2:1 ((a)(i):((a)(ii)+(a)(iii))).

6. The composition of claim 4 having a pH of 5 to 9.

7. The composition of claim 4 in the form of a gel.

8. The composition of claim 4 comprising:
   (c) 1 to 40 wt. % of one or more fatty compounds; and
   (d) 0.1 to 10 wt. % of one or more emulsifiers.

9. The composition of claim 8, wherein the one or more fatty compounds are chosen from non-silicone fatty compounds.

10. The composition of claim 8, wherein the one or more emulsifiers are chosen from glyceryl esters and derivatives, alkoxylated carboxylic acids, oxyalkylenated fatty acid esters of glycerol, oxyalkylenated fatty acid esters of sorbitan, oxyalkylenated fatty acid esters, oxyalkylenated fatty alkyl ethers, sugar esters, and mixtures thereof.

11. The composition of claim 8 in the form of an emulsion.

12. The composition of claim 4, further comprising:
   (e) 1 to 40 wt. % of one or more water-soluble solvents.

13. The composition of claim 12, wherein the one or more water-soluble solvents are chosen from a glycol, glycerin, a C1-C4 alcohol, a polyhydric alcohol, and a mixture thereof.

14. The composition of claim 4 having a viscosity of 5,000 cP to about 100,000 cP at 25° C.

15. The composition of claim 4, further comprising:
   (f) one or more skin active agents.

16. The composition of claim 1 comprising:
   (a)(i) 0.1 to 8 wt. % of the carbomer;
   (a)(ii) 0.1 to 5 wt. % of the acrylates/C10-30 alkyl acrylate crosspolymer;
   (a)(iii) 0.1 to 5 wt. % of the ammonium acryloyldimethyltaurate/steareth-25 methacrylate crosspolymer; and
   (b) 60 to 90 wt. % of the water;
   wherein (a)(i) and ((a)(ii)+(a)(iii)) are in a weight ratio of 0.8:1 to 1.3:1 ((a)(i):((a)(ii)+(a)(iii))), and the composition comprises 0.1 to 10 wt. % of the polymer blend.

17. A method for treating skin comprising applying a cosmetic composition of claim 1 to the skin.

18. A rheological-modifying and stabilizing polymer blend comprising:
   (i) about 40 to 60 wt. % of a carbomer;
   (ii) about 22 to 28 wt. % of an acrylates/C10-30 alkyl acrylate crosspolymer; and
   (iii) about 22 to 28 wt. % of an ammonium acryloyldimethyltaurate/steareth-25 methacrylate crosspolymer;
      wherein all weight percentages are based on the total weight of the rheological-modifying and stabilizing polymer blend; and wherein (i) and ((ii)+(iii)) are in a weight ratio of 0.5:1 to 2:1 ((i):((ii)+(iii))).

19. The composition of claim 1, which is essentially free of crosslinked siloxane elastomers.

20. The composition of claim 1, which is essentially free of silicones.

* * * * *